US006995182B2

(12) United States Patent
Mutel et al.

(10) Patent No.: US 6,995,182 B2
(45) Date of Patent: Feb. 7, 2006

(54) 1-SULFONYL PYRROLIDINE DERIVATIVES

(75) Inventors: Vincent Mutel, Mulhouse (FR); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 68 days.

(21) Appl. No.: 10/397,908

(22) Filed: Mar. 26, 2003

(65) Prior Publication Data

US 2003/0212066 A1    Nov. 13, 2003

Related U.S. Application Data

(62) Division of application No. 09/880,539, filed on Jun. 13, 2001, now Pat. No. 6,589,978.

(30) Foreign Application Priority Data

Jun. 30, 2000   (EP)   .................................. 00113894

(51) Int. Cl.
*A61K 31/40* (2006.01)
*A61K 31/4196* (2006.01)
*C07D 207/04* (2006.01)
*C07D 249/08* (2006.01)

(52) U.S. Cl. ...................... 514/383; 548/131; 548/143; 548/215; 548/250; 548/262.2; 548/311.1; 548/314.7; 548/364.1; 548/542; 514/374; 514/381; 514/424

(58) Field of Classification Search ................ 548/542, 548/131, 143, 215, 250, 262.2, 311.1, 314.7, 548/364.1; 514/424, 381, 383, 374
See application file for complete search history.

(56) References Cited

U.S. PATENT DOCUMENTS 3,905,979 A * 9/1975 Henry et al. ................. 546/122
4,539,411 A * 9/1985 Broger et al. ............... 548/402
5,036,153 A * 7/1991 Braish et al. ............... 548/542
6,143,776 A * 11/2000 Erlanson ..................... 514/424
6,284,785 B1   9/2001 Mutel et al.
6,469,036 B1 * 10/2002 Costanzo et al. ........... 514/359
6,645,939 B1 * 11/2003 Durette et al. ................ 514/19
6,649,763 B1 * 11/2003 Yoon et al. ................. 546/156

FOREIGN PATENT DOCUMENTS

| WO | WO 97/48681 | 12/1997 |
| WO | WO 98/35675 | 8/1998 |
| WO | WO 99/26615 | 6/1999 |
| WO | WO 99/45006 | 9/1999 |
| WO | WO 99/62888 | 12/1999 |
| WO | WO 00/37458 | 6/2000 |
| WO | WO 00/58285 | 10/2000 |

OTHER PUBLICATIONS

Holladay et al (1999): STN International CAPLUS database, Columbus (Ohio), Accession No., 1999: 421682.*
P. Bravo et al., *Tetrahedron Letters*, vol. 40, pp. 6317-6320 (1999).
Pascal Coric et al., *J. Med. Chem.*, vol. 39, pp. 2594-2608 (1996).
Carmen Najera etal., *Tetrahedron Asymmetry*, vol. 10, pp. 2245-2303 (1999).
E. J. Schlager and K.Christensen, *Cytotechnology*, vol. 30, pp. 71-83 (1999).
Wouter et al., *Synlett*, pp. 1079-1080 (Sep. 1997).
B. J. Littler et al., *Synlett*, vol. 1, pp. 22-24 (1997).
Katzsukiyo et al., *Organic Letters*, vol. 2, No. 3, pp. 385-388 (2000).

* cited by examiner

*Primary Examiner*—Golam M. M. Shameem
(74) *Attorney, Agent, or Firm*—George W. Johnston; Patricia S. Rocha-Tramaloni; Kimberly J. Prior

(57) ABSTRACT

The present invention is a series of compounds that are derivatives of 1-sulfonyl-pyrrolidine and that demonstrate affinity towards metabotropic glutamate receptors. The invention further relates to medicaments containing these compounds and to a process for their preparation. The compounds possess affinity towards metabotropic glutamate receptors and are therefore useful in the treatment or prevention of acute and/or chronic neurological disorders.

144 Claims, No Drawings

1-SULFONYL PYRROLIDINE DERIVATIVES

This application is a divisional of U.S. patent application Ser. No. 09/880,539, filed Jun. 13, 2001 now U.S. Pat. No. 6,589,978.

FIELD OF INVENTION

The present invention is generally related to 1-sulfonyl pyrrolidine derivitives showing affinity toward metabotropic glutamate receptors.

BACKGROUND

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

SUMMARY

The present invention is a compound of the formula

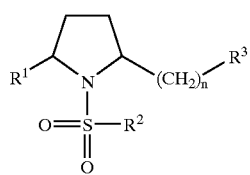

wherein
$R^1$ signifies hydrogen or aryl, which is unsubstituted or substituted by halogen;
$R^2$ signifies aryl, which is unsubstituted or substituted by halogen or lower alkyl;
$R^3$ signifies —OR', cyano, halogen, N-hydroxy-amidino, —C(O)—OR, —C(O)NR'R", —N(R')—C(O)—$R^4$, —N(R')—S(O)$_2$—R, —N(R')—C(S)—NR'"R or a 5- or 6-membered heteroaryl ring containing 1 to 4 N or O heteroatoms, said ring being unsubstituted or substituted by lower alkyl or cycloalkyl;
$R^4$ signifies cycloalkyl, phenyl or lower alkyl, which is unsubstituted or substituted by halogen;
R signifies lower alkyl;
R' and R'" signify hydrogen, lower alkyl or cycloalkyl-lower alkyl;
R" signifies hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl;
n is an integer from 0 to 5;

or its pharmaceutically acceptable salts.

It has been surprisingly found that the compounds of formula I possess affinity towards metabotropic glutamate receptors. Compounds of formula I are distinguished by valuable therapeutic properties.

Objects of the present invention are compounds of formula I and pharmaceutically acceptable salts thereof, racemic mixtures and their corresponding enantiomers, the above-mentioned compounds as pharmaceutically active substances, their manufacture, medicaments based on a compound in accordance with the invention and their production as well as the use of the compounds in accordance with the invention in the control or prevention of illnesses of the aforementioned kind, and, respectively, for the production of corresponding medicaments.

DETAILED DESCRIPTION

The present invention includes a compound of the formula

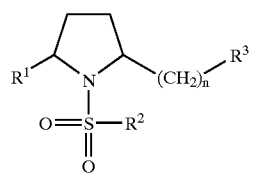

wherein
$R^1$ signifies hydrogen or aryl, which is unsubstituted or substituted by halogen;
$R^2$ signifies aryl, which is unsubstituted or substituted by halogen or lower alkyl;
$R^3$ signifies —OR', cyano, halogen, N-hydroxy-amidino, —C(O)—OR, —C(O)NR'R", —N(R')—C(O)—$R^4$, —N(R')—S(O)$_2$—R, —N(R')—C(S)—NR'"R or a 5- or 6-membered heteroaryl ring containing from 1 to 4 N or O heteroatoms, said ring being unsubstituted or substituted by lower alkyl or cycloalkyl;
$R^4$ signifies cycloalkyl, phenyl or lower alkyl, which is unsubstituted or substituted by halogen;
R signifies lower alkyl;

R' and R''' signify hydrogen, lower alkyl or cycloalkyl-lower alkyl;

R'' signifies hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and n is an integer from 0 to 5;

or pharmaceutically acceptable salts thereof.

Preferred compounds of formula I include a compound wherein $R^1$ is hydrogen; $R^2$ is aryl unsubstituted or substituted by halogen or lower alkyl; $R^3$ and n are as defined above. An additional preferred compound includes a compound wherein $R^2$ is p-tolyl and n is 3. Yet an additional preferred compound includes $R^3$ as N(R')—C(O)—$R^4$, or 5- or 6-membered heteroaryl groups containing 1 to 4 heteroatoms selected independently from each other from N or O, which are unsubstituted or substituted by lower alkyl or cycloalkyl, and $R^4$ is as defined above.

A further preferred compound has the structure

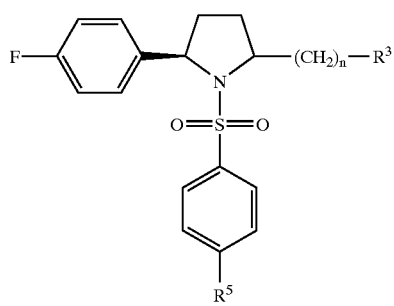

I-A wherein $R^3$ and n are as above; and wherein $R^5$ is hydrogen, halogen or lower alkyl. Additionally, compound I-A wherein $R^3$ is —OR', N-hydroxy-amidino, —C(O)NR'R'' or —N(R')—C(O)—$R^4$; $R^5$ is halogen and n is 2 or 3 is preferred. Compound I-A is also preferred when $R^3$ is OR'; $R^5$ is ethyl; R' is as above and n is 1. Another preferred compound of formula I-A includes $R^3$ being a 5- or 6-membered heteroaryl ring containing from 1 to 4 heteroatoms selected independently from each other from N or O, which is unsubsituted or substituted by lower alkyl or cycloalkyl with n as an integer between 0 and 5.

Another preferred compound of the present invention has the structure

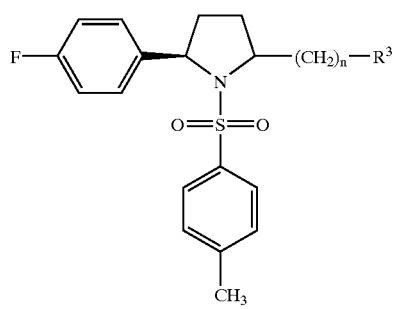

I-B wherein $R^3$ and n are as above.

A compound of formula I-B when $R^3$ is an unsubstituted 5-membered heteroaryl group containing from 1 to 4 heteroatoms selected independently from each other from N or O is also preferred. Yet another preferred compound of formula I-B includes $R^3$ as an unsubstituted 5-membered heteroaryl group containing from 1 to 4 nitrogen atoms and n is 0, 1 or 2. A compound of formula I-B is also preferred when the heteroaryl group includes at least one oxygen and n is 0, 1 or 2 or when n is 3, 4 or 5. An additional preferred compound of formula I-B includes $R^3$ being a substituted 5-membered heteroaryl group containing 1 to 4 heteroatoms selected independently from each other from N or O; the 5-membered heteroaryl group containing from 1 to 4 nitrogen atoms with n as 0, 1 or 2; or the case where the substituted 5-membered heteroaryl group contains from 1 to 4 nitrogen atoms and n is 3, 4 or 5. An additional preferred compound of formula I-B includes $R^3$ being a substituted 5-membered heteroaryl group containing 1 to 4 heteroatoms selected from N or O and containing at least one N and at least one O wherein n is 0, 1 or 2; or when n is 3, 4, or 5.

Yet another preferred compound of formula I-B includes $R^3$ being selected from —C(O)—OR, —C(O)NR'R'', cyano, halogen, N-hydroxy-amidino, —N(R')—C(O)—$R^4$, —C(O)—OR, —N(R')—S($O_2$)—R and —N(R')—C(S)—NR'''R, wherein R', R'', R''', $R^4$ and R are as defined above.

Another preferred compound of formula I has the structure

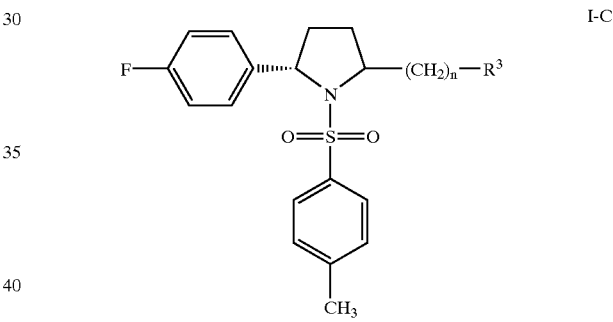

I-C wherein $R^3$ and n are as defined above. Another preferred compound of formula I-C includes $R^3$ being —N(R')—C(O)—$R^4$; wherein $R^4$ and R' are as defined above with n being 0, 1 or 2 or additionally when n is 3, 4 or 5. Yet another preferred compound of formula IV includes $R^3$ being —N(R')—C(O)—$R^4$; wherein $R^4$ and R' are as defined above; and n is 3, 4 or 5. A further preferred compound of formula I-C includes $R^3$ being —C(O)NR'R'', wherein R' and R'' are as defined above.

An additional preferred compound of formula IV includes $R^3$ being 5- or 6-membered heteroaryl groups containing from 1 to 4 heteroatoms selected independently from each other from N or O, which are unsubstituted or substituted by lower alkyl or cycloalkyl.

One further preferred compound of formula IV includes $R^3$ being a substituted 5-membered heteroaryl group with n being 0, 1 or 2, or with n being 3, 4 or 5. Another preferred compound of formula I-C includes $R^3$ being an unsubstituted 5-membered heteroaryl group with n being 0, 1 or 2 or the case when n is 3, 4 or 5. One more preferred compound of formula I-C includes $R^3$ being —OR' with R' is as above and n is 0, 1 or 2, or 3, 4 or 5.

Preferred compounds of formula I in the scope of the present invention are those, in which $R^3$ signifies 5- or 6-membered heteroaryl groups containing from 1 to 4 heteroatoms selected independently from each other from N or O, which are optionally substituted by lower alkyl or cycloalkyl.

Especially preferred are compounds of formula I, wherein the heteroaryl group is selected from imidazole, pyrazole, [1,2,4]triazole, [1,2,4]oxadiazole or tetrazole, which is optionally substituted by lower alkyl or cycloalkyl.

The following are examples of such compounds:
(2RS,5SR)-5-{2-[5-(4-fluoro-phenyl)-1-(toluene-4-sulfonyl)-pyrrolidin-2-yl]-ethyl}-3-methyl-[1,2,4]oxadiazole,
(2RS,5SR)-5-[5-(4-fluoro-phenyl)-1-(toluene-4-sulfonyl)-pyrrolidin-2-yl-methyl]-2-methyl-2H-tetrazole,
(2RS,5RS)-5-{3-[5-(4-fluoro-phenyl)-1-(toluene-4-sulfonyl)-pyrrolidin-2-yl]-propyl}-2-methyl-2H-tetrazole,
(2RS,5RS)-5-{4-[5-(4-fluoro-phenyl)-1-(toluene-4-sulfonyl)-pyrrolidin-2-yl]-butyl}-1-methyl-1H-tetrazole,
(2R,5S)-5-{2-[5-(4-fluoro-phenyl)-1-(toluene-4-sulfonyl)-pyrrolidin-2-yl]-ethyl}-2-methyl-2H-tetrazole,
(2R,5S)-5-{2-[5-(4-fluoro-phenyl)-1-(toluene-4-sulfonyl)-pyrrolidin-2-yl]-ethyl}-1-methyl-1H-tetrazole,
(2RS,5RS)-5-{3-[5-(4-fluoro-phenyl)-1-(toluene-4-sulfonyl)-pyrrolidin-2-yl]-propyl}-1-methyl-1H-[1,2,4]triazole,
(2RS,5SR)-5-{2-[5-(4-fluoro-phenyl)-1-(toluene-4-sulfonyl)-pyrrolidin-2-yl]-ethyl}-1-methyl-1H-[1,2,4]triazole,
(2RS,5SR)-3-{2-[5-(4-fluoro-phenyl)-1-(toluene-4-sulfonyl)-pyrrolidin-2-yl]-ethyl}-1-methyl-1H-[1,2,4]triazole,
(2RS,5RS)-1-{3-[5-(4-fluoro-phenyl)-1-(toluene-4-sulfonyl)-pyrrolidin-2-yl]-propyl}-1H-[1,2,4]triazole,
(2RS,5RS)-1-{3-[5-(4-fluoro-phenyl)-1-(toluene-4-sulfonyl)-pyrrolidin-2-yl]-propyl}-1H-imidazole,
(2RS,5RS)-1-{3-[5-(4-fluoro-phenyl)-1-(toluene-4-sulfonyl)-pyrrolidin-2-yl]-propyl}-1H-pyrazole,
(2RS,5RS)-1-{3-[5-(4-fluoro-phenyl)-1-(toluene-4-sulfonyl)-pyrrolidin-2-yl]-propyl}-1H-tetrazole,
(2RS,5SR)-3-cyclopropyl-5-[5-(4-fluoro-phenyl)-1-(toluene-4-sulfonyl)-pyrrolidin-2-ylmethyl]-[1,2,4]oxadiazole,
(2RS,5SR)-1-{2-[5-(4-fluoro-phenyl)-1-(toluene-4-sulfonyl)-pyrrolidin-2-yl]-ethyl}-1H-[1,2,4]triazole,
(2R,5S)-1-{3-[5-(4-fluoro-phenyl)-1-(toluene-4-sulfonyl)-pyrrolidin-2-yl]-propyl}-1H-[1,2,4]triazole,
(2S,5S)-1-{3-[5-(4-fluoro-phenyl)-1-(toluene-4-sulfonyl)-pyrrolidin-2-yl]-propyl}-1H-imidazole,
(2S,5S)-1-{3-[5-(4-fluoro-phenyl)-1-(toluene-4-sulfonyl)-pyrrolidin-2-yl]-propyl}-1H-pyrazole,
(2S,5S)-5-{3-[5-(4-fluoro-phenyl)-1-(toluene-4-sulfonyl)-pyrrolidin-2-yl]-propyl}-1-methyl-1H-[1,2,4]triazole,
(2RS,5RS)-1-{4-[5-(4-fluoro-phenyl)-1-(toluene-4-sulfonyl)-pyrrolidin-2-yl]-butyl}-1H-[1,2,4]triazole,
(2RS,5RS)-2-{4-[5-(4-fluoro-phenyl)-1-(toluene-4-sulfonyl)-pyrrolidin-2-yl]-butyl}-2H-tetrazole,
(2S,5S)-1-{4-[5-(4-fluoro-phenyl)-1-(toluene-4-sulfonyl)-pyrrolidin-2-yl]-butyl}-1H-imidazole, or
(2S,5S)-1-{4-[5-(4-fluoro-phenyl)-1-(toluene-4-sulfonyl)-pyrrolidin-2-yl]-butyl}-1H-[1,2,4]triazole.

Further preferred compounds of formula I are those, wherein the heteroaryl group is selected from [1,3,4]oxadiazole or oxazole, which is optionally substituted by lower alkyl or cycloalkyl.

The following are examples of such compounds:
(2RS,5SR)-2-{2-[5-(4-fluoro-phenyl)-1-(toluene-4-sulfonyl)-pyrrolidin-2-yl]-ethyl}[1,3,4]oxadiazole,
(2RS,5SR)-2-{2-[5-(4-fluoro-phenyl)-1-(toluene-4-sulfonyl)-pyrrolidin-2-yl]-ethyl}-5-methyl-[1,3,4]oxadiazole,
(2RS,5SR)-5-{2-[5-(4-fluoro-phenyl)-1-(toluene-4-sulfonyl)-pyrrolidin-2-yl]-ethyl}-oxazole,
(2RS,5RS)-2-{3-[5-(4-fluoro-phenyl)-1-(toluene-4-sulfonyl)-pyrrolidin-2-yl]-propyl}[1,3,4]oxadiazole, or
(2RS,5RS)-2-{3-[5-(4-fluoro-phenyl)-1-(toluene-4-sulfonyl)-pyrrolidin-2-yl]-propyl}-5-methyl-[1,3,4]oxadiazole.

Further preferred are compounds of formula I, in which $R^3$ signifies —N(R')—C(O)—$R^4$ and
$R^4$ signifies cycloalkyl or lower alkyl, which is optionally substituted by halogen.

The following are examples of such compounds:
(2RS,5SR)-cyclopropanecarboxylic acid [5-(4-fluoro-phenyl)-1-(toluene-4-sulfonyl)-pyrrolidin-2-yl-methyl]-amide,
(2SR,5SR)-cyclopropanecarboxylic acid {3-[5-(4-fluoro-phenyl)-1-(toluene-4-sulfonyl)-pyrrolidin-2-yl]-propyl}-amide,
(2S,5S)-cyclopropanecarboxylic acid {3-[5-(4-fluoro-phenyl)-1-(toluene-4-sulfonyl)-pyrrolidin-2-yl]-propyl}-amide,
(2SR,5SR)-N-{3-[5-(4-fluoro-phenyl)-1-(toluene-4-sulfonyl)-pyrrolidin-2-yl]-propyl}-acetamide,
(2RS,5RS)-N-{3-[5-(4-fluoro-phenyl)-1-(toluene-4-sulfonyl)-pyrrolidin-2-yl]-propyl}-propionamide,
(2RS,5RS)-N-{4-[5-(4-fluoro-phenyl)-1-(toluene-4-sulfonyl)-pyrrolidin-2-yl]-butyl}-acetamide,
(2RS,5RS)-N-{5-[5-(4-fluoro-phenyl)-1-(toluene-4-sulfonyl)-pyrrolidin-2-yl]-pentyl}-acetamide,
(2S,5S)-N-{3-[5-(4-fluoro-phenyl)-1-(toluene-4-sulfonyl)-pyrrolidin-2-yl]-propyl}-acetamide,
(2RS,5RS)-2,2,2-trifluoro-N-{3-[5-(4-fluoro-phenyl)-1-(toluene-4-sulfonyl)-pyrrolidin-2-yl]-propyl}-acetamide, or
(2RS,5RS)-N-{3-[5-(4-fluoro-phenyl)-1-(toluene-4-sulfonyl)-pyrrolidin-2-yl]-propyl}-isobutyramide.

Also preferred are compounds of formula I, in which
$R^3$ signifies —OR' and
R' signifies hydrogen or methyl.

The following are examples of such compounds:
(2RS,5RS)-3-[5-(4-fluoro-phenyl)-1-(toluene-4-sulfonyl)-pyrrolidin-2-yl]-propan-1-ol,
(2S,5S)-3-[5-(4-fluoro-phenyl)-1-(toluene-4-sulfonyl)-pyrrolidin-2-yl]-propan-1-ol,
(2RS,5SR)-2-(4-fluoro-phenyl)-5-(2-methoxy-ethyl)-1-(toluene-4-sulfonyl)-pyrrolidine,
(2RS,5RS)-2-(4-fluoro-phenyl)-5-(3-methoxy-propyl)-1-(toluene-4-sulfonyl)-pyrrolidine,
(2RS,5RS)-4-[5-(4-fluoro-phenyl)-1-(toluene-4-sulfonyl)-pyrrolidin-2-yl]-butan-1-ol, or
(2S,5S)-2-(4-fluoro-phenyl)-5-(4-methoxy-butyl)-1-(toluene-4-sulfonyl)-pyrrolidine.

Further preferred are compounds of formula I, in which
$R^3$ signifies —C(O)NR'R" and
R' signifies hydrogen or lower alkyl and
R" signifies hydrogen, lower alkyl or lower alkyl substituted by a 5- or 6-membered heteroaryl group containing 1 to 4 heteroatoms selected from N or O, which is optionally substituted by lower alkyl or cycloalkyl.

The following are examples of such compounds:
(2RS,5RS)-5-[5-(4-fluoro-phenyl)-1-(toluene-4-sulfonyl)-pyrrolidin-2-yl]-pentanoic acid amide, or
(2R,5S)-3-[5-(4-fluoro-phenyl)-1-(toluene-4-sulfonyl)-pyrrolidin-2-yl]-propionamide.

Compounds of formula I, in which
R³ signifies —N(R')—S(O)₂—R and
R signifies lower alkyl and
R' signifies hydrogen, lower alkyl or lower alkyl substituted by a 5- or 6-membered heteroaryl group containing 1 to 4 heteroatoms selected from N or O, which is optionally substituted by lower alkyl or cycloalkyl, are also preferred.

(2RS,5RS)-N-{3-[5-(4-fluoro-phenyl)-1-(toluene-4-sulfonyl)-pyrrolidin-2-yl]-propyl}-methanesulfonamide is an example of such a compound.

The invention embraces all stereoisomeric forms in addition to the racemates.

The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, t-butyl and the like.

The term "cycloalkyl" denotes a saturated carbocyclic group containing from 3 to 7 carbon atoms, preferred are cyclopropyl and cyclopentyl.

The term "cycloalkyl-lower alkyl" denotes a lower alkyl residue as defined above which is substituted by a cycloalkyl group as defined above, preferred is cyclopropylmethyl.

The term "halogen" denotes fluorine, chlorine, bromine and iodine.

The term "aryl" means the monovalent aromatic carbocyclic radical consisting of one individual ring, or one or more fused rings in which at least one ring is aromatic in nature. Preferred aryl groups are phenyl or naphthyl.

The term "heteroaryl" means the monovalent aromatic cyclic radical incorporating one or more heteroatoms. The term "5- or 6-membered heteroaryl rings containing from 1 to 4 N or O heteroatoms" embraces furyl, pyrrolyl, 1H-imidazolyl, 2H-imidazolyl, 4H-imidazolyl, 1H-pyrazolyl, 3H-pyrazolyl, 4H-pyrazolyl, 1,2-oxazolyl, 1,3-oxazolyl, 1H-[1,2,4]triazolyl, 4H-[1,2,4]triazolyl, 1H-[1,2,3]triazolyl, 2H-[1,2,3]triazolyl, 4H-[1,2,3]triazolyl, [1,2,4]oxadiazolyl, [1,3,4]oxadiazolyl, [1,2,3]oxadiazolyl, 1H-tetrazolyl, 2H-tetrazolyl, [1,2,3,4]oxatriazolyl, [1,2,3,5]oxatriazolyl, 1H-pentazolyl, pyridyl, pyrazinyl, pyrimidinyl, pyridazinyl and their dihydro derivatives. The heteroaryl ring is optionally substituted by lower alkyl or cycloalkyl.

Preferred are the following 5-membered heteroaryl rings: 1H-imidazolyl, 1H-pyrazolyl, 1H-[1,2,4]triazolyl, [1,2,4]oxadiazolyl, 4,5-dihydro-[1,2,4]oxadiazolyl, [1,3,4]oxadiazolyl, oxazolyl, 1H-tetrazolyl and 2H-tetrazolyl.

Preferred 6-membered heteroaryl groups are pyridyl or pyrimidyl.

The compounds of formula I and their pharmaceutically acceptable salts can be manufactured by reacting a compound of the formula

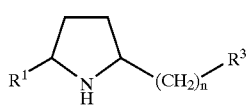

II with a compound of formula

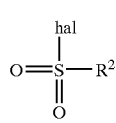

III to obtain a compound of formula

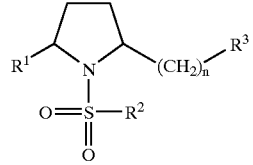

I and, if desired, converting a functional group of R³ in a compound of formula I into another functional group, and if desired, converting a compound of formula I into a pharmaceutically acceptable salt.

Compounds of formula I may also be obtained directly by simply exchanging the functional group at position R³ by another functional group.

In accordance with the invention, an appropriately substituted compound of formula II, for example methyl (2RS, 5SR)-5-(4-fluorophenyl)-1-pyrrolidine-2-carboxylate, is reacted with a suitable compound of formula III, for example toluene-4-sulfonyl chloride and triethylamine (see Scheme 1). R¹, R³ and n have the significance given earlier. The reaction according to known methods is carried out at room temperature within 16 hours in an inert solvent, for example in dichloromethane.

Scheme 1

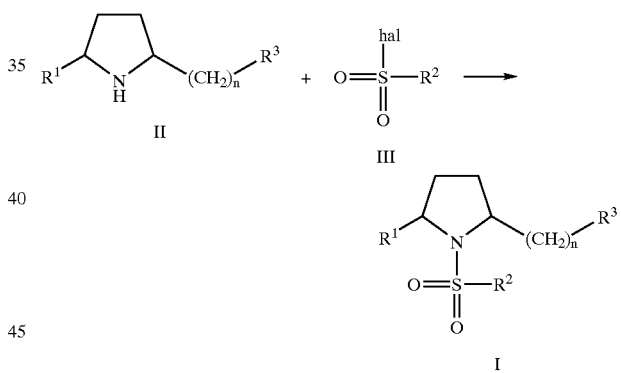

A compound of formula II is prepared by reacting a suitable compound of formula V with diethyl acetaminomalonate (IV) followed by hydrogenation on platinum oxide according to Scheme 2 or, for the case when R¹ is H (see Example 84), DL-proline methyl ester can be used as starting material.

Scheme 2

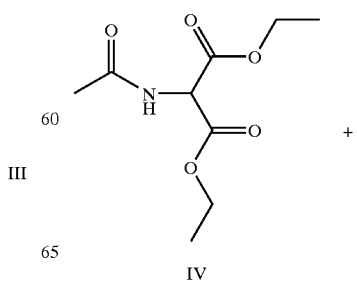

IV

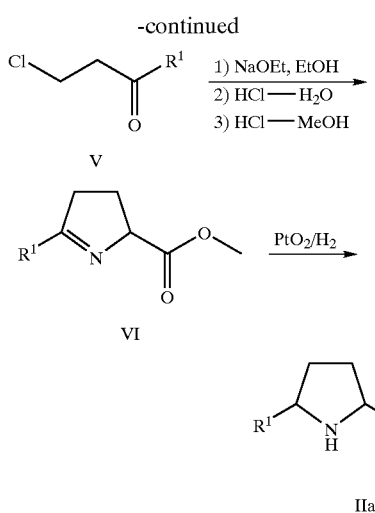

A stereoselective synthesis of a compound of formula II can be achieved by reacting optically pure N-Boc-pyroglutamate with (4-fluoro-phenyl)magnesium bromide according to the methods described in Tetrahedron Letters 34, 6317–6320, 1999, J. Med. Chem. 39, 2594–2608, 1996 and Tetrahedron: Asymmetry 10, 2245–2303, 1999.

Scheme 3 shows how prolongation of the side chain starting with a compound of formula Ia, for example (2RS, 5SR)-5-(4-fluoro-phenyl)-1-(toluene-4-sulfonyl)-pyrrolidine-2-carboxylic acid methyl ester (Example 1), can be achieved. For instance, after reduction with lithium aluminium hydride to the corresponding alcohol, mesylation and nucleophilic substitution by cyanide compounds of formula Ic having a side chain with 2 C-atoms are obtained. Compounds of formula Ia1 containing 3 C-atoms in the side chain are prepared by oxidation of the alcohol to the aldehyde VII followed by Wittig reaction and hydrogenation.

Scheme 3

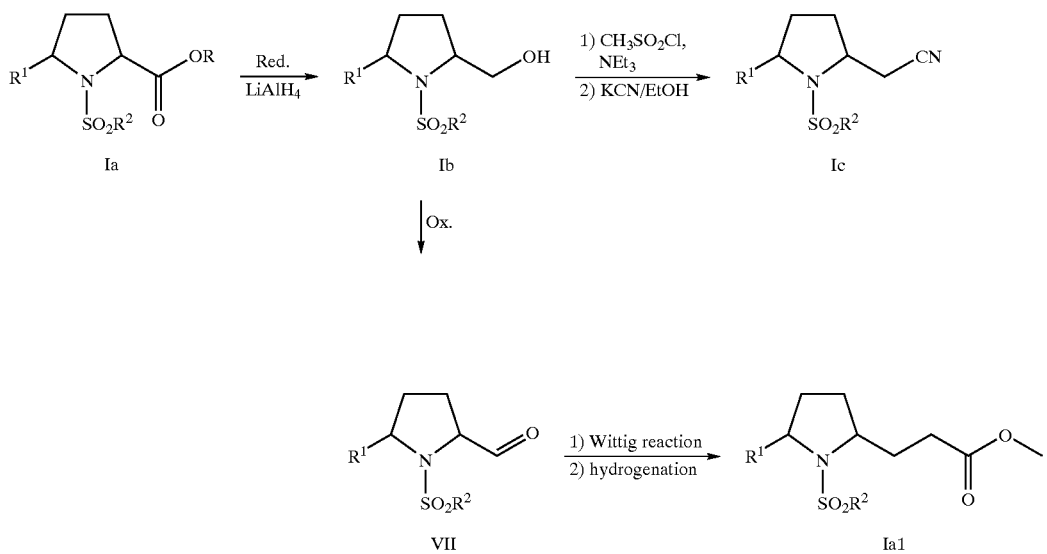

Tetrazolyl derivatives of formula If (e.g. Examples 27, 39, 40, 49, 50) can be prepared by a 1,3-dipolar addition of sodium azide to a nitrile of formula Ic1. The nitrile is preferably obtained by converting the ester group of a compound of formula Ia2 into the amide and dehydrating the amide with phosphorus oxychloride. Methyl-1,2,4-Triazolyl derivatives of formula Ig (e.g. examples 26, 69, 70) can be manufactured by addition of methylhydrazine to the nitrile. The cyano group of a compound of formula Ic1 can further be hydrogenated to the corresponding amine, which may be acylated with a suitable acylchloride to obtain a compound of formula Ie (e.g. examples 9, 15, 16). The acylation is preferably carried out with pyridine in dichloromethane. An overview of these reactions is given in Scheme 4 below. $R^4$ has the significance given earlier.

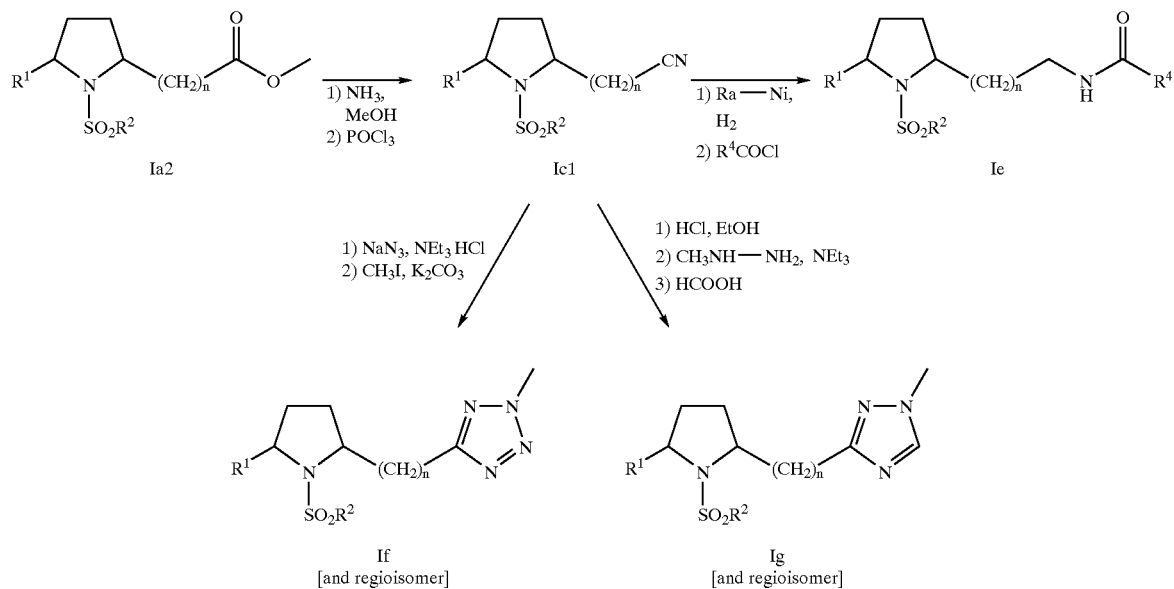

Scheme 4

The formation of a 1,2,4-oxadiazolyl ring can be achieved by condensation of an acid of formula VIII with N-hydroxy-acetamidine as follows: a solution of the acid and 1,1'-carbonyl-diimidazole is stirred in DMF at room temperature for 2 h. N-hydroxy-acetamidine is then added and the reaction mixture is heated to 80° C. for 16 h. After evaporation and solvation in acetic acid the reaction mixture is heated under reflux conditions for 2 h and after purification using known methods a compound of formula Ih (e.g. Example 25) is obtained (see Scheme 5).

1,2,4-Oxadiazolyl derivatives of formula Ij (e.g. Example 13) can be manufactured from the nitrile of formula Ic1 by reaction with hydroxylamine hydrochloride to obtain the carboxamidine Ii, which is condensed with acetic acid in DMF in the presence of 1,1'-carbonyl-diimidazole to form the 1,2,4-oxadiazolyl ring.

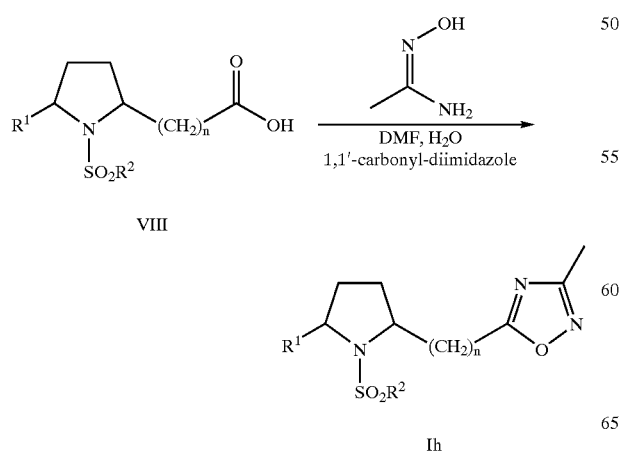

Scheme 5

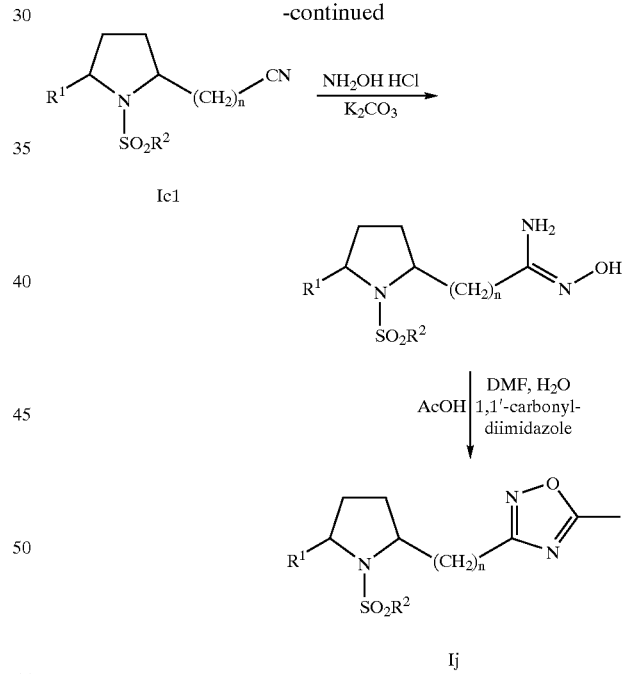

The hydroxyl group of a compound of formula Ib1 can be methylated by known methods to obtain a compound of formula Im or substituted by a halogen atom. For example, reaction with thionylchloride yields the corresponding chloralkyl derivative (Ik). The halogen atom can further be substituted with a cyclic amine, for example 1,2,4-triazol (see Example 82), with the help of sodium hydride at 0° C. The product, a compound of formula Il, is purified by known methods. In Scheme 6, X signifies, independently from each other, a N-atom or a C-atom.

Scheme 6

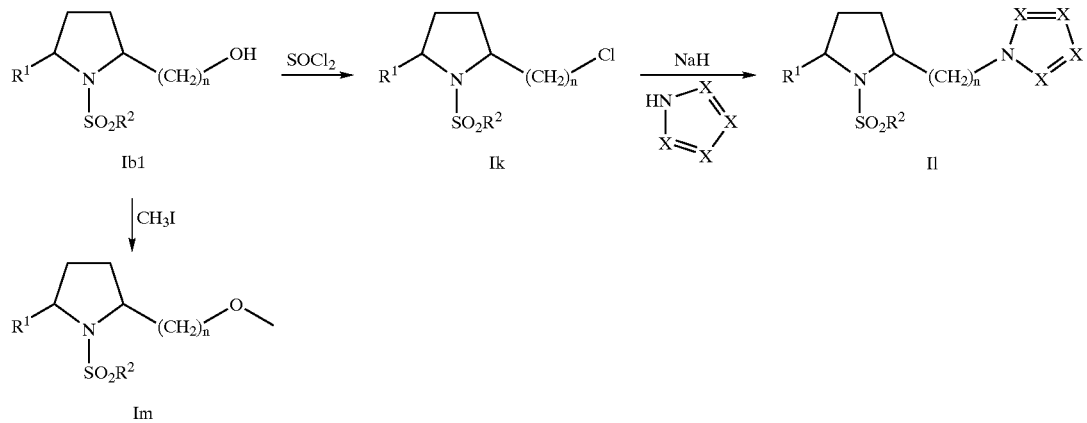

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts possess, as already mentioned above, affinity towards metabotropic glutamate receptors (group 1 mGlu receptors) and can be used for the treatment or prevention of acute and/or chronic neurological disorders, such as psychosis, schizophrenia, Alzheimer's disease, cognitive disorders and memory deficits, as well as acute and chronic pain. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Alzheimer's disease, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The pharmacological activity of the compounds was tested using the following method: cDNA encoding rat mGlu 1a receptor was transiently transfected into EBNA cells using a procedure described by E.-J. Schlaeger and K. Christensen (Transient gene expression in mammalian cells grown in serum-free suspension culture; Cytotechnology, 15: 1–13, 1998). [$Ca^{2+}$]i measurements were performed on mGlu 1a transfected EBNA cells after incubation of the cells with Fluo-3 AM (0.5 $\mu$M final concentration) for 1 hour at 37° C. followed by 4 washes with assay buffer (DMEM supplemented with Hank's salt and 20 mM HEPES. [$Ca^{2+}$]i measurements were done using a fluorometric imaging plate reader (FLIPR, Molecular Devices Corporation, La Jolla, Calif., USA). When compounds were evaluated as antagonists they were tested against 10 $\mu$M glutamate as agonist.

The inhibition (antagonists) or activation (agonists) curves were fitted with a four parameter logistic equation giving $EC_{50}$, $IC_{50}$, and Hill coefficient using the iterative non linear curve fitting software Origin (Microcal Software Inc., Northampton, Mass., USA).

The compounds of the present invention are group 1 mGlu receptor agonists. All of the compounds of the invention show activities, as measured in the assay described above, of 10 $\mu$M or less, typically 1 $\mu$M or less, and ideally of 0.3 $\mu$M or less.

In the table below are shown some specific activity data:

| Example No. | Compound name | $EC_{50}$ ($\mu$M) |
|---|---|---|
| 4 | (2RS,5SR)-5-(4-fluoro-phenyl)-1-(toluene-4-sulfonyl)-pyrrolidine-2-carbonitrile | 4.40 |
| 5 | (2RS,5SR)-2-chloromethyl-5-(4-fluoro-phenyl)-1-(toluene-4-sulfonyl)-pyrrolidine | 1.40 |
| 16 | (2RS,5SR)-cyclopropanecarboxylic acid[5-(4-fluoro-phenyl)-1-(toluene-4-sulfonyl)-pyrrolidin-2-yl-methyl]-amide | 0.21 |
| 21 | (2RS,5SR)-3-[5-(4-fluoro-phenyl)-1-(toluene-4-sulfonyl)-pyrrolidin-2-yl-methyl]-5-methyl-[1,2,4]oxadiazole | 0.63 |
| 39 | (2RS,5SR)-5-[5-(4-fluoro-phenyl)-1-(toluene-4-sulfonyl)-pyrrolidin-2-yl-methyl]-2-methyl-2H-tetrazole | 0.36 |
| 64 | (2S,5S)-3-[5-(4-fluoro-phenyl)-1-(toluene-4-sulfonyl)-pyrrolidin-2-yl]-propan-1-ol | 0.20 |
| 77 | (2RS,5RS)-N-{3-[5-(4-fluoro-phenyl)-1-(toluene-4-sulfonyl)-pyrrolidin-2-yl]-propyl}-methanesulfonamide | 0.16 |
| 87 | (RS)-cyclopropanecarboxylic acid{3-[1-(toluene-4-sulfonyl)-pyrrolidin-2-yl]-propyl}-amide | 0.98 |
| 101 | (2RS,5SR)-2-{2-[5-(4-fluoro-phenyl)-1-(toluene-4-sulfonyl)-pyrrolidin-2-yl]-ethyl}-2H-tetrazole | 1.47 |
| 116 | (2S,5S)-1-{3-[5-(4-fluoro-phenyl)-1-(toluene-4-sulfonyl)-pyrrolidin-2-yl]-propyl}-1H-imidazole | 0.22 |
| 123 | (2RS,5RS)-2-{3-[5-(4-fluoro-phenyl)-1-(toluene-4-sulfonyl)-pyrrolidin-2-yl]-propyl}-4,6-dimethyl-pyrimidine | 1.28 |

-continued

| Example No. | Compound name | EC$_{50}$ ($\mu$M) |
|---|---|---|
| 137 | (2RS,5SR)-2-[5-(4-fluoro-phenyl)-1-(toluene-4-sulfonyl)-pyrrolidin-2-yl]-[1,3,4]oxadiazole | 1.24 |
| 143 | (2RS,5RS)-2-{4-[5-(4-fluoro-phenyl)-1-(toluene-4-sulfonyl)-pyrrolidin-2-yl]-butyl}-2H-tetrazole | 0.35 |

The compounds of formula I or the pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants and the like. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

EXAMPLE 1

(2RS,5SR)-5-(4-Fluoro-phenyl)-1-(toluene-4-sulfonyl)-pyrrolidine-2-carboxylic acid methyl ester a) Diethyl acetamido[2-(4-fluorobenzoyl)-ethyl]malonate To a stirred solution of diethyl acetaminomalonate (4.34 g, 0.02 mol) in EtOH (30 ml) was added at room temperature sodium ethanolate (1.46 g, 20.4 mmol) and subsequently 3-chloro-4'-fluoro-propiophenone (3.73 g, 0.02 mol). The reaction mixture was heated under reflux conditions for 5 h, poured onto ice-water (70 ml), acidified (25 ml 3N sulfuric acid) and extracted with ethyl acetate (2×100 ml). The combined organic layers were washed with brine (70 ml), dried (MgSO$_4$) and evaporated to give a brown oil (7.95 g). Crystallization from ethyl acetate/hexane yielded diethyl acetamido[2-(4-fluorobenzoyl)-ethyl]malonate (5.72 g, yield 78%) as an off-white solid, m.p. 73° C.

b) Methyl (RS)-2-(4-fluorophenyl)-1-pyrroline-5-carboxylate

A stirred solution of diethyl acetamido[2-(4-fluorobenzoyl)-ethyl]malonate (5.72 g, 15.6 mmol) in conc. hydrochloric acid (45 ml) was heated under reflux conditions for 15 h, filtered and evaporated. Subsequently hydrochloric acid in MeOH (3N, 30 ml) was added and the solution stirred at room temperature for 20 h. The reaction mixture was evaporated, sat. NaHCO$_3$ solution was added (50 ml) and the aqueous phase was extracted with ethyl acetate (2×100 ml). The combined organic layers were washed with brine (70 ml), dried (MgSO4) and evaporated to give methyl (RS)-2-(4-fluorophenyl)-1-pyrroline-5-carboxylate (2.3 g, yield 67%) as a pale brown oil, MS: m/e=221 (M$^+$).

c) Methyl (2RS,5SR)-5-(4-fluorophenyl)-1-pyrrolidine-2-carboxylate

Hydrogenation of methyl (RS)-2-(4-fluorophenyl)-1-pyrroline-5-carboxylate (2.3 g, 10.4 mmol) on platinum oxide (260 mg) in MeOH (120 ml) for 3 h at room temperature yielded methyl (2RS,5SR)-5-(4-fluorophenyl)-1-pyrrolidine-2-carboxylate (2.27 g, yield 98%) as a light brown oil, MS: m/e=224.2 (M+H$^+$).

d) (2RS,5SR)-5-(4-Fluoro-phenyl)-1-(toluene-4-sulfonyl)-pyrrolidine-2-carboxylic acid methyl ester To a stirred solution of methyl (2RS,5SR)-5-(4-fluoro-phenyl)-pyrrolidine-2-carboxylate (2.27 g, 10.2 mmol) and triethylamine (2.13 ml, 15.3 mmol) in dichloromethane (60 ml) was added at 0° C. toluene-4-sulfonyl chloride (2.32 g, 12.2 mmol). The mixture was stirred at RT for 16 h, evaporated, dissolved in water (50 ml) and extracted with dichloromethane (2×40 ml). The combined organic layers were washed with water (40 ml), brine (40 ml), dried (MgSO$_4$) and evaporated. The crude product was purified by crystallization from diethyl ether/hexane to give the title compound, off-white solid, m.p. 91° C. and MS: m/e=378.3 (M+H$^+$).

EXAMPLE 2

(2RS,5SR)-[5-(4-Fluoro-phenyl)-1-(toluene-4-sulfonyl)-pyrrolidin-2-yl]-methanol

Reduction of (2RS,5SR)-5-(4-fluoro-phenyl)-1-(toluene-4-sulfonyl)-pyrrolidine-2-carboxylic acid methyl ester with lithium aluminum hydride (1.5 eq.) in THF at RT, aqueous work-up and crystallization from diethyl ether/hexane yielded the title compound, white solid, m.p. 82° C. and MS: m/e=350 (M+H$^+$).

EXAMPLE 3

(2RS,5SR)-5-(4-Fluoro-phenyl)-1-(toluene-4-sulfonyl)-pyrrolidine-2-carboxylic acid amide A solution of (2RS,5SR)-5-(4-fluoro-phenyl)-1-(toluene-4-sulfonyl)-pyrrolidine-2-carboxylic acid methyl ester (1.3 g, 3.44 mmol) in MeOH (75 ml) and ammonium hydroxide solution (50 ml, 25%) was stirred at room temperature for 72 h. The volume of the solution was reduced to 50 ml and water (150 ml) was added. The title compound precipitated as a white solid (0.95 g, yield 76%), m.p. 137° C. and MS: m/e=363.1 (M+H$^+$).

EXAMPLE 4

(2RS,5SR)-5-(4-Fluoro-phenyl)-1-(toluene-4-sulfonyl)-pyrrolidine-2-carbonitrile

A stirred mixture of (2RS,5SR)-5-(4-fluoro-phenyl)-1-(toluene-4-sulfonyl)-pyrrolidine-2-carboxylic acid amide (1.15 g, 3.17 mmol) and phosphorus oxide chloride (8 ml) was heated for 5 min under reflux conditions. Aqueous work-up and crystallization from ethyl acetate/hexane yielded the title compound as a light brown solid (0.9 g, yield 82%), m.p. 128° C. and MS: m/e=344 (M$^+$).

EXAMPLE 5

(2RS,5SR)-2-Chloromethyl-5-(4-fluoro-phenyl)-1-(toluene-4-sulfonyl)-pyrrolidine

A stirred mixture of (2RS,5SR)-[5-(4-fluoro-phenyl)-1-(toluene-4-sulfonyl)-pyrrolidin-2-yl]-methanol (1.25 g, 3.58 mmol) and thionyl chloride (2 ml) was heated for 4 h at 80° C. aqueous work-up and crystallization from ethyl acetate/hexane yielded the title compound as an off-white solid (1.12 g, yield 85%), m.p. 130° C. and MS: m/e=367 (M$^+$).

EXAMPLE 6

(2RS,5SR)-5-(4-Fluoro-phenyl)-1-(toluene-4-sulfonyl)-pyrrolidine-2-carboxylic acid (pyridin-3-yl-methyl)-amide hydrochloride a) (2RS,5SR)-5-(4-fluoro-phenyl)-1-(toluene-4-sulfonyl)-pyrrolidine-2-carboxylic acid A solution of (2RS,5SR)-5-(4-fluoro-phenyl)-1-(toluene-4-sulfonyl)-pyrrolidine-2-carboxylic acid methyl ester (4.35 g, 11.5 mmol) in 1N potassium hydroxide solution (100 ml) was stirred at room temperature for 17 h. Aqueous work-up yielded (2RS,5SR)-5-(4-fluoro-phenyl)-1-(toluene-4-sulfonyl)-pyrrolidine-2-carboxylic acid (4.05 g, yield 97%) as a white solid, m.p. 166° C.

b) (2RS,5SR)-5-(4-fluoro-phenyl)-1-(toluene-4-sulfonyl)-pyrrolidine-2-carboxylic chloride To a stirred suspension of (2RS,5SR)-5-(4-fluoro-phenyl)-1-(toluene-4-sulfonyl)-pyrrolidine-2-carboxylic acid (4.05 g, 11.1 mmol) in toluene (60 ml) was added thionyl chloride (1.21 ml, 16.7 mmol) and the mixture was stirred at 80° C. for 1.5 h. Evaporation of the solvent yielded (2RS,5SR)-5-(4-fluoro-phenyl)-1-(toluene-4-sulfonyl)-pyrrolidine-2-carboxylic chloride as a light brown solid.

c) (2RS,5SR)-5-(4-Fluoro-phenyl)-1-(toluene-4-sulfonyl)-pyrrolidine-2-carboxylic acid (pyridin-3-yl-methyl)-amide hydrochloride To a stirred and cooled (0° C.) solution of (2RS,5SR)-5-(4-fluoro-phenyl)-1-(toluene-4-sulfonyl)-pyrrolidine-2-carboxylic chloride (764 mg, 2 mmol) in dichloromethane (30 ml) was added pyridine (0.16 ml, 2 mmol) and 3-picolylamine (0.18 ml, 1.8 mmol). The reaction mixture was stirred at room temperature for 22 h. Aqueous work-up, formation of the hydrochloride (3N MeOH/HCl) and crystallization (diethyl ether) yielded the title compound (0.69 g, yield 70%) as a white solid, m.p. 186° C. and MS: m/e=454.5 (M+H$^+$).

EXAMPLE 7

(2RS,5SR)-5-(4-Fluoro-phenyl)-N-hydroxy-1-(toluene-4-sulfonyl)-pyrrolidine-2-carboxamidine To a stirred suspension of (2RS,5SR)-5-(4-fluoro-phenyl)-1-(toluene-4-sulfonyl)-pyrrolidine-2-carbonitrile (0.74 g, 2.15 mmol) in EtOH (25 ml) was added potassium carbonate (0.89 g, 6.45 mmol) and hydroxylamine hydrochloride (0.30 g, 4.30 mmol). The reaction mixture was heated under reflux conditions for 18 h, the formed precipitate collected, washed with dichloromethane/methanol. The organic solvents were evaporated and the crude product purified by column chromatography on silica gel (ethyl acetate/hexane 3:2). Crystallization from diethyl ether/methanol yielded the title compound (0.31 g, yield 38%) as a white solid, m.p. 217° C. and MS: m/e=378.3 (M+H$^+$).

EXAMPLE 8

(2RS,5SR)-2-(4-Fluoro-phenyl)-5-methoxymethyl-1-(toluene-4-sulfonyl)-pyrrolidine To a stirred and cooled (0° C.) solution of (2RS,5SR)-[5-(4-fluoro-phenyl)-1-(toluene-4-sulfonyl)-pyrrolidin-2-yl]-methanol in THF (10 ml) was added sodium hydride (147 mg, 3.66 mmol, 60%) and the reaction mixture was stirred at room temperature for 1 h. Subsequently methyl iodide (0.34 ml, 5.5 mmol) was added at 0° C. and stirring was continued for 3 h at room temperature. Aqueous work-up and crystallization from ethyl acetate/hexane yielded the title compound as a white solid (0.53 g, yield 79%), m.p. 152° C. and MS: m/e=364.3 (M+H$^+$).

EXAMPLE 9

(2RS,5SR)-N-[5-(4-Fluoro-phenyl)-1-(toluene-4-sulfonyl)-pyrrolidin-2-yl-methyl]-acetamide a) (2RS,5SR)-[5-(4-fluoro-phenyl)-1-(toluene-4-sulfonyl)-pyrrolidin-2-yl]]-methylamine Hydrogenation of (2RS,5SR)-5-(4-fluoro-phenyl)-1-(toluene-4-sulfonyl)-pyrrolidine-2-carbonitrile (1.22 g, 3.54 mmol) in 7N MeOH/NH$_3$ at RT with Ra—Ni as catalyst yielded (2RS,5SR)-[5-(4-fluoro-phenyl)-1-(toluene-4-sulfonyl)-pyrrolidin-2-yl]-methylamine (1.06 g, yield 86%) as a pale yellow oil.

b) (2RS,5SR)-N-[5-(4-Fluoro-phenyl)-1-(toluene-4-sulfonyl)-pyrrolidin-2-yl-methyl]-acetamide Acetylation of (2RS,5SR)-[5-(4-fluoro-phenyl)-1-(toluene-4-sulfonyl)-pyrrolidin-2-yl]-methylamine according to the general method of example 6c and crystallization from ethyl acetate/hexane yielded the title compound as a white solid, m.p. 117° C. and MS: m/e=391.2 (M+H$^+$).

EXAMPLE 10

(2RS,5SR)-[5-(4-Fluoro-phenyl)-1-(toluene-4-sulfonyl)-pyrrolidin-2-yl]-acetonitrile Reaction of (2RS,5SR)-[5-(4-fluoro-phenyl)-1-(toluene-4-sulfonyl)-pyrrolidin-2-yl]-methanol (2.15 g, 6.15 mmol) and methanesulfonyl chloride (0.57 ml, 7.38 mmol) in accordance with the general method of example 1d yielded the corresponding (2RS,5SR)-[5-(4-fluoro-phenyl)-1-(toluene-4-sulfonyl)-pyrrolidin-2-yl]-methanesulfonate (2.60 g, 99%), which was subsequently heated with potassium cyanide (0.61 g, 9.43 mmol) in EtOH/water (95:5; 130 ml) under reflux conditions for 24 h. Aqueous work-up and column chromatography on silica gel (ethyl acetate/hexane 2:3) gave the starting material (1.02 g, 47%) and the title compound (0.64 g, yield 29%) as an off-white solid, m.p. 116° C. and MS: m/e=359.2 (M+H$^+$).

EXAMPLE 11

(2RS,5SR)-[1-(4-Ethyl-benzenesulfonyl)-5-(4-fluoro-phenyl)-pyrrolidin-2-yl]-methanol The title compound, pale yellow oil, MS: m/e=363 (M$^+$) was prepared in accordance with the general methods of example 1d and 84a from methyl (2RS,5SR)-5-(4-fluoro-phenyl)-pyrrolidine-2-carboxylate and 4-ethyl-benzenesulfonyl chloride and subsequent reduction of methyl (2RS,5SR)-5-(4-fluoro-phenyl)-1-(4-ethyl-benzenesulfonyl)-pyrrolidine-2-carboxylate with lithium aluminum hydride according to the general method of example 2.

EXAMPLE 12

(2RS,5SR)-2-[5-(4-Fluoro-phenyl)-1-(toluene-4-sulfonyl)-pyrrolidin-2-yl]-N-hydroxy-acetamidine The title compound, off-white solid, m.p. 84° C. and MS: m/e=390.3 (M+H$^+$) was prepared in accordance with the general method of example 7 from (2RS,5SR)-[5-(4-fluoro-phenyl)-1-(toluene-4-sulfonyl)-pyrrolidin-2-yl]-acetonitrile.

EXAMPLE 13

(2RS,5SR)-3-[5-(4-Fluoro-phenyl)-1-(toluene-4-sulfonyl)-pyrrolidin-2-yl]-5-methyl-[1,2,4]oxadiazole A solution of acetic acid (0.11 ml, 1.99 mmol), 1,1'-carbonyl-diimidazole (0.32 g, 1.99 mmol) in DMF (12 ml) was stirred at room temperature for 2 h and subsequently (2RS,5SR)-5-(4-fluoro-phenyl)-N-hydroxy-1-(toluene-4-sulfonyl)-pyrrolidine-2-carboxamidine (0.50 g, 1.32 mmol) was added. The reaction mixture was stirred at 80° C. for 16 h and evaporated. Acetic acid (10 ml) was added and the stirred mixture was heated under reflux conditions for 2 h. Aqueous work-up, column chromatography on silica gel (ethyl acetate/hexane 1:1) and crystallization from ethyl acetate/hexane yielded the title compound (0.36 g, yield 68%) as a white solid, m.p. 115° C. and MS: m/e=246.1 (M+H$^+$).

EXAMPLE 14

(2RS,5SR)-3-[5-(4-Fluoro-phenyl)-1-(toluene-4-sulfonyl)-pyrrolidin-2-yl]-[1,2,4]oxadiazole A stirred solution of (2RS,5SR)-5-(4-fluoro-phenyl)-N-hydroxy-1-(toluene-4-sulfonyl)-pyrrolidine-2-carboxamidine (0.49 g, 1.3 mmol) in triethyl orthoformate (20 ml) was heated under reflux conditions for 2.5 h. Aqueous work-up, column chromatography on silica gel (toluene/ethyl acetate 4:1) and crystallization from ethyl acetate/hexane yielded the title compound (0.11 g, yield 22%) as a white solid, m.p. 165° C. and MS: m/e=387 (M$^+$).

EXAMPLE 15

(2RS,5SR)-N-[5-(4-Fluoro-phenyl)-1-(toluene-4-sulfonyl)-pyrrolidin-2-yl-methyl]-propionamide Acylation of (2RS,5SR)-[5-(4-fluoro-phenyl)-1-(toluene-4-sulfonyl)-pyrrolidin-2-yl]-methylamine according to the general method of example 6c and crystallization from ethyl acetate/hexane yielded the title compound as a white solid, m.p. 142° C. and MS: m/e=405.4 (M+H$^+$).

EXAMPLE 16

(2RS,5SR)-Cyclopropanecarboxylic acid [5-(4-fluoro-phenyl)-1-(toluene-4-sulfonyl)-pyrrolidin-2-yl-methyl]-amide Acylation of (2RS,5SR)-[5-(4-fluoro-phenyl)-1-(toluene-4-sulfonyl)-pyrrolidin-2-yl]-methylamine according to the general method of example 6c and crystallization from ethyl acetate/hexane yielded the title compound as a white solid, m.p. 154° C. and MS: m/e=417.3 (M+H$^+$).

EXAMPLE 17

(2RS,5SR)-N-{2-[5-(4-Fluoro-phenyl)-1-(toluene-4-sulfonyl)-pyrrolidin-2-yl]-ethyl}-propionamide Hydrogenation of (2RS,5SR)-[5-(4-fluoro-phenyl)-1-(toluene-4-sulfonyl)-pyrrolidin-2-yl]-acetonitrile according to the general method of example 9a and subsequent acylation of the corresponding (2RS,5SR)-[5-(4-fluoro-phenyl)-1-(toluene-4-sulfonyl)-pyrrolidin-2-yl]-ethylamine in accordance with the general method of example 6c yielded the title compound as a colorless oil, MS: m/e=419.4 (M+H$^+$).

EXAMPLE 18

(2RS,5SR)-N-{2-[5-(4-Fluoro-phenyl)-1-(toluene-4-sulfonyl)-pyrrolidin-2-yl]-ethyl}-benzamide Acylation of (2RS,5SR)-[5-(4-fluoro-phenyl)-1-(toluene-4-sulfonyl)-pyrrolidin-2-yl]-ethylamine according to the general method of example 6c and crystallization from ethyl acetate/hexane yielded the title compound as a light brown solid, m.p. 60° C. and MS: m/e=467.3 (M+H+).

EXAMPLE 19

(2RS,5SR)-Cyclopropanecarboxylic acid {2-[5-(4-fluoro-phenyl)-1-(toluene-4-sulfonyl)-pyrrolidin-2-yl]-ethyl}-amide Acylation of (2RS,5SR)-[5-(4-fluoro-phenyl)-1-(toluene-4-sulfonyl)-pyrrolidin-2-yl]-ethylamine according to the general method of example 6c and column chromatography on silica gel yielded the title compound as a colorless oil, MS: m/e=431.5 (M+H+).

EXAMPLE 20

(2RS,5SR)-N-{2-[5-(4-Fluoro-phenyl)-1-(toluene-4-sulfonyl)-pyrrolidin-2-yl]-ethyl}-acetamide Acetylation of (2RS,5SR)-[5-(4-fluoro-phenyl)-1-(toluene-4-sulfonyl)-pyrrolidin-2-yl]-ethylamine according to the general method of example 6c and crystallization from ethyl acetate/hexane yielded the title compound as a white solid, m.p. 124° C. and MS: m/e=405.4 (M+H+).

EXAMPLE 21

(2RS,5SR)-3-[5-(4-Fluoro-phenyl)-1-(toluene-4-sulfonyl)-pyrrolidin-2-yl-methyl]-5-methyl-[1,2,4] oxadiazole The title compound, pale yellow oil, MS: m/e=416.3 (M+H+) was prepared in accordance with the general method of example 13 from (2RS,5SR)-2-[5-(4-fluoro-phenyl)-1-(toluene-4-sulfonyl)-pyrrolidin-2-yl]-N-hydroxy-acetamidine and acetic acid.

EXAMPLE 22

(2RS,5SR)-5-Cyclopropyl-3-[5-(4-fluoro-phenyl)-1-(toluene-4-sulfonyl)-pyrrolidin-2-yl-methyl]-[1,2,4] oxadiazole The title compound, pale yellow oil, MS: m/e=442.3 (M+H+) was prepared in accordance with the general method of example 13 from (2RS,5SR)-2-[5-(4-fluoro-phenyl)-1-(toluene-4-sulfonyl)-pyrrolidin-2-yl]-N-hydroxy-acetamidine and cyclopropyl-carboxylic acid.

EXAMPLE 23

(2RS,5SR)-3-[5-(4-Fluoro-phenyl)-1-(toluene-4-sulfonyl)-pyrrolidin-2-yl-methyl]-[1,2,4]oxadiazole The title compound, colorless oil, MS: m/e=402.0 (M+H+) was prepared in accordance with the general method of example 14 from (2RS,5SR)-2-[5-(4-fluoro-phenyl)-1-(toluene-4-sulfonyl)-pyrrolidin-2-yl]-N-hydroxy-acetamidine.

EXAMPLE 24

(2RS,5SR)-5-Phenyl-1-(toluene-4-sulfonyl)-pyrrolidine-2-carboxylic acid amide

The title compound, white solid, m.p. 130° C. and MS: m/e=300.1 (M+H+) was prepared in accordance with the general method of example 3 from (2RS,5SR)-5-phenyl-1-(toluene-4-sulfonyl)-pyrrolidine-2-carboxylic acid methyl ester, which was prepared in accordance with the general method of example 1d from (2RS,5SR)-5-phenyl-pyrrolidine-2-carboxylic acid methyl ester and toluene-4-sulfonyl chloride.

EXAMPLE 25

(2RS,5SR)-5-[5-(4-Fluoro-phenyl)-1-(toluene-4-sulfonyl)-pyrrolidin-2-yl]-3-methyl-[1,2,4] oxadiazole The title compound, off-white solid, m.p. 128° C. and MS: m/e=401.2 (M+) was prepared in accordance with the general method of example 13 from (2RS,5SR)-5-(4-fluoro-phenyl)-1-(toluene-4-sulfonyl)-pyrrolidine-2-carboxylic acid and N-hydroxy-acetamidine.

EXAMPLE 26

(2RS,5SR)-3-[5-(4-Fluoro-phenyl)-1-(toluene-4-sulfonyl)-pyrrolidin-2-yl]-1-methyl-1H-[1,2,4] triazole To a freshly prepared solution of hydrochloric acid in EtOH (10 ml) was added at 0° C. (2RS,5SR)-5-(4-fluoro-phenyl)-1-(toluene-4-sulfonyl)-pyrrolidine-2-carbonitrile (0.50 g, 1.45 mmol), the reaction mixture was stirred at room temperature for 1.5 h and evaporated. The light brown solid (0.65 g) was dissolved in EtOH (10 ml), methylhydrazine (86.9 mg, 1.89 mmol) and triethylamine (0.51 ml, 3.63 mmol) were added and the mixture was stirred at room temperature for 2 h. The reaction mixture was evaporated, subsequently dissolved in formic acid (10 ml), stirred at room temperature for 0.5 h and heated under reflux conditions for 1.5 h. Evaporation, aqueous work-up, column chromatography on silica gel (ethyl acetate) and crystallization from ethyl acetate/hexane yielded the title compound (0.37 g, yield 64%) as a white solid, m.p. 160° C. and MS: m/e=400 (M+).

EXAMPLE 27

(2RS,5SR)-5-[5-(4-Fluoro-phenyl)-1-(toluene-4-sulfonyl)-pyrrolidin-2-yl]-2-methyl-2H-tetrazole a) (2RS,5SR)-5-[5-(4-fluoro-phenyl)-1-(toluene-4-sulfonyl)-pyrrolidin-2-yl]-2H-tetrazole To a stirred solution of (2RS,5SR)-5-(4-fluoro-phenyl)-1-(toluene-4-sulfonyl)-pyrrolidine-2-carbonitrile (0.70 g, 2.03 mmol) in DMF (25 ml) was added at room temperature sodium azide (0.40 g, 6.10 mmol) and triethylamine hydrochloride (0.42 g, 3.05 mmol) and the reaction mixture was stirred at 120° C. for 6 h. The mixture was poured in water (100 ml), acidified (2 N HCl) and the formed solid was collected to give (2RS,5SR)-5-[5-(4-fluoro-phenyl)-1-(toluene-4-sulfonyl)-pyrrolidin-2-yl]-2H-tetrazole (0.73 g, yield 93%) as an off-white solid, m.p. 150° C.

b) (2RS,5SR)-5-[5-(4-Fluoro-phenyl)-1-(toluene-4-sulfonyl)-pyrrolidin-2-yl]-2-methyl-2H-tetrazole To a stirred solution of (2RS,5SR)-5-[5-(4-fluoro-phenyl)-1-(toluene-4-sulfonyl)-pyrrolidin-2-yl]-2H-tetrazole (0.72 g, 1.86 mmol) in acetone (30 ml) was added at room temperature potassium carbonate (0.51 g, 3.72 mmol) and methyl iodide (0.23 ml, 3.72 mmol) and the reaction mixture was heated under reflux conditions for 3 h. Aqueous work-up, column chromatography on silica gel (ethyl acetate/hexane 2:3) and crystallization from ethyl acetate/hexane yielded the title compound (0.44 g, 59%) as a white solid, m.p. 150° C. and MS: m/e=402.4 (M+H$^+$). As second product of this reaction (2RS,5SR)-5-[5-(4-fluoro-phenyl)-1-(toluene-4-sulfonyl)-pyrrolidin-2-yl]-1-methyl-1H-tetrazole (0.26 g, yield 35%) was obtained as a white solid, m.p. 186° C. and MS: m/e=402.4 (M+H$^+$).

EXAMPLE 28

3-[5-(4-Fluoro-phenyl)-1-(toluene-4-sulfonyl)-pyrrolidin-2-yl]-5-methyl-4,5-dihydro-[1,2,4]oxadiazole (mixture of Diastereoisomers; 2,5-cis)

To a stirred suspension of (2RS,5SR)-2-[5-(4-fluoro-phenyl)-1-(toluene-4-sulfonyl)-pyrrolidin-2-yl]-N-hydroxy-acetamidine (0.4 g, 1.06 mmol) in EtOH (12.5 ml)/water (10 ml) was added acetaldehyde (4.2 ml, 74.4 mmol) and the reaction mixture was heated under reflux conditions for 8 h. Evaporation of the solvent, aqueous work-up yielded the crude product (0.5 g) as a colorless oil. Further purification by column chromatography on silica gel (ethyl acetate/hexane 3:2) and crystallization from ethyl acetate/hexane gave the title compound as a white solid, m.p. 68° C. and MS: m/e=404.4 (M+H$^+$).

EXAMPLE 29

(2RS,5SR)-3-[5-(4-Fluoro-phenyl)-1-(toluene-4-sulfonyl)-pyrrolidin-2-yl]-propionamide a) (2RS,5SR)-5-(4-fluoro-phenyl)-1-(toluene-4-sulfonyl)-pyrrolidine-2-carboxaldehyde
To a stirred solution of (2RS,5SR)-[5-(4-fluoro-phenyl)-1-(toluene-4-sulfonyl)-pyrrolidin-2-yl]-methanol (8.12 g, 23.2 mmol) in dichloromethane (150 ml) was added triethylamine (16.2 ml, 116 mmol). To the cooled solution (0° C.) was added dropwise over a period of 15 min pyridine-SO$_3$-complex (18.3 g, 116 mmol) dissolved in DMSO (75 ml) and the reaction mixture was stirred for 1 h at 0° C. Aqueous work-up yielded (2RS,5SR)-5-(4-fluoro-phenyl)-1-(toluene-4-sulfonyl)-pyrrolidine-2-carboxaldehyde (8.0 g, yield 99%) as a light brown oil.

b) (2RS,5SR)-3-[5-(4-fluoro-phenyl)-1-(toluene-4-sulfonyl)-pyrrolidin-2-yl]-propionic acid methyl ester
To a cooled (0° C.) and stirred suspension of sodium hydride (1.29 g, 32.2 mmol; 60%) in THF (60 ml) was added over a period of 20 min trimethyl phosphonoacetate (5.31 ml, 36.8 mmol) in THF (40 ml). After 30 min a solution of (2RS,5SR)-5-(4-fluoro-phenyl)-1-(toluene-4-sulfonyl)-pyrrolidine-2-carboxaldehyde (8.0 g, 23.0 mmol) in THF (40 ml) was added dropwise over a period of 25 min and the reaction mixture was subsequently stirred at 55° C. for 2 h. Aqueous work-up and further purification by column chromatography on silica gel (toluene/ethyl acetate 9:1) yielded the product as a colorless oil (5.77 g, 62%), which was subsequently dissolved in MeOH (200 ml) and hydrogenated at room temperature on Pd-C (10%, 0.6 g) over a period of 1.5 h to give (2RS,5SR)-3-[5-(4-fluoro-phenyl)-1-(toluene-4-sulfonyl)-pyrrolidin-2-yl]-propionic acid methyl ester (5.35 g, yield 92%) as a colorless oil.

c) (2RS,5SR)-3-[5-(4-Fluoro-phenyl)-1-(toluene-4-sulfonyl)-pyrrolidin-2-yl]-propionamide
The title compound, off-white solid, m.p. 136° C. and MS: m/e=391.2 (M+H$^+$) was prepared in accordance with the general method of example 3 from (2RS,5SR)-3-[5-(4-fluoro-phenyl)-1-(toluene-4-sulfonyl)-pyrrolidin-2-yl]-propionic acid methyl ester.

EXAMPLE 30

(2RS,5SR)-5-{2-[5-(4-Fluoro-phenyl)-1-(toluene-4-sulfonyl)-pyrrolidin-2-yl]-ethyl}-3-methyl-[1,2,4] oxadiazole The title compound, white solid, m.p. 91° C. and MS: m/e=430.5 (M$^+$) was prepared in accordance with the general method of example 13 from N-hydroxy-acetamidine and (2RS,5SR)-3-[5-(4-fluoro-phenyl)-1-(toluene-4-sulfonyl)-pyrrolidin-2-yl]-propionic acid, which was prepared in accordance with the general method of example 6a from (2RS,5SR)-3-[5-(4-fluoro-phenyl)-1-(toluene-4-sulfonyl)-pyrrolidin-2-yl]-propionic acid methyl ester.

EXAMPLE 31

(2RS,5SR)-3-[5-(4-Fluoro-phenyl)-1-(toluene-4-sulfonyl)-pyrrolidin-2-yl]-propionitrile The title compound, white solid, m.p. 86° C. and MS: m/e=373.1 (M+H$^+$) was prepared in accordance with the general method of example 4 from (2RS,5SR)-3-[5-(4-fluoro-phenyl)-1-(toluene-4-sulfonyl)-pyrrolidin-2-yl]-propionamide.

EXAMPLE 32

(2SR,5SR)-N-{3-[5-(4-Fluoro-phenyl)-1-(toluene-4-sulfonyl)-pyrrolidin-2-yl]-propyl}-acetamide Hydrogenation of (2RS,5SR)-[5-(4-fluoro-phenyl)-1-(toluene-4-sulfonyl)-pyrrolidin-2-yl]-propionitrile according to the general method of example 9a and subsequent acetylation of the corresponding (2SR,5SR)-[5-(4-fluoro-phenyl)-1-(toluene-4-sulfonyl)-pyrrolidin-2-yl]-propylamine in accordance with the general method of example 6c yielded the title compound as a colorless oil, MS: m/e=419.3 (M+H$^+$).

EXAMPLE 33

(2SR,5SR)-Cyclopropanecarboxylic acid {3-[5-(4-fluoro-phenyl)-1-(toluene-4-sulfonyl)-pyrrolidin-2-yl]-propyl}-amide Acylation of (2SR,5SR)-[5-(4-fluoro-phenyl)-1-(toluene-4-sulfonyl)-pyrrolidin-2-yl]-propylamine according to the general method of example 6c yielded the title compound as a colorless oil, MS: m/e=445.5 (M+H$^+$).

EXAMPLE 34

(2RS,5SR)-3-[5-(4-Fluoro-phenyl)-1-(toluene-4-sulfonyl)-pyrrolidin-2-yl]-N-hydroxy-propionamidine The title compound, off-white solid, m.p. 134° C. and MS: m/e=406.4 (M+H$^+$) was prepared in accordance with the general method of example 7 from (2RS,5SR)-[5-(4-fluoro-phenyl)-1-(toluene-4-sulfonyl)-pyrrolidin-2-yl]-propionitrile.

EXAMPLE 35

(2RS,5SR)-5-Cyclopropyl-3-{2-[5-(4-fluoro-phenyl)-1-(toluene-4-sulfonyl)-pyrrolidin-2-yl]-ethyl}-[1,2,4]oxadiazole The title compound, pale brown oil, MS: m/e=455 (M$^+$) was prepared in accordance with the general method of example 13 from (2RS,5SR)-2-[5-(4-fluoro-phenyl)-1-(toluene-4-sulfonyl)-pyrrolidin-2-yl]-N-hydroxy-propionamidine and cyclopropyl-carboxylic acid.

EXAMPLE 36

(2RS,5SR)-3-{2-[5-(4-Fluoro-phenyl)-1-(toluene-4-sulfonyl)-pyrrolidin-2-yl]-ethyl}-5-methyl-[1,2,4]oxadiazole The title compound, pale brown oil, MS: m/e=430.1 (M+H$^+$) was prepared in accordance with the general method of example 13 from (2RS,5SR)-2-[5-(4-fluoro-phenyl)-1-(toluene-4-sulfonyl)-pyrrolidin-2-yl]-N-hydroxy-propionamidine and acetic acid.

EXAMPLE 37

(2RS,5SR)-Cyclopentanecarboxylic acid [5-(4-fluoro-phenyl)-1-(toluene-4-sulfonyl)-pyrrolidin-2-yl-methyl]-amide Acylation of (2RS,5SR)-[5-(4-fluoro-phenyl)-1-(toluene-4-sulfonyl)-pyrrolidin-2-yl]-methylamine according to the general method of example 6c and crystallization from ethyl acetate/hexane yielded the title compound as an off-white solid, m.p. 147° C. and MS: m/e=445.3 (M+H$^+$).

EXAMPLE 38

(2RS,5SR)-N-[5-(4-Fluoro-phenyl)-1-(toluene-4-sulfonyl)-pyrrolidin-2-yl-methyl]-2,2-dimethyl-propionamide Acylation of (2RS,5SR)-[5-(4-fluoro-phenyl)-1-(toluene-4-sulfonyl)-pyrrolidin-2-yl]-methylamine according to the general method of example 6c and crystallization from hexane yielded the title compound as a white solid, m.p. 128° C. and MS: m/e=433.4 (M+H$^+$).

EXAMPLE 39

(2RS,5SR)-5-[5-(4-Fluoro-phenyl)-1-(toluene-4-sulfonyl)-pyrrolidin-2-yl-methyl]-2-methyl-2H-tetrazole The title compound, colorless oil, MS: m/e=416.1 (M+H$^+$) was prepared in accordance with the general method of example 27a/b from (2RS,5SR)-[5-(4-fluoro-phenyl)-1-(toluene-4-sulfonyl)-pyrrolidin-2-yl]-acetonitrile.

A second product of this reaction was (2RS,5SR)-5-[5-(4-fluoro-phenyl)-1-(toluene-4-sulfonyl)-pyrrolidin-2-yl-methyl]-1-methyl-1H-tetrazole, colorless oil, MS: m/e=416.3 (M+H$^+$).

EXAMPLE 40

(2RS,5SR)-5-{2-[5-(4-Fluoro-phenyl)-1-(toluene-4-sulfonyl)-pyrrolidin-2-yl]-ethyl}-2-methyl-2H-tetrazole The title compound, colorless oil, MS: m/e=430.4 (M+H$^+$) was prepared in accordance with the general method of example 27a/b from (2RS,5SR)-[5-(4-fluoro-phenyl)-1-(toluene-4-sulfonyl)-pyrrolidin-2-yl]-propionitrile.

A second product of this reaction was (2RS,5SR)-5-{2-[5-(4-fluoro-phenyl)-1-(toluene-4-sulfonyl)-pyrrolidin-2-yl]-ethyl}-1-methyl-1H-tetrazole, colorless oil, MS: m/e=430.1 (M+H$^+$).

EXAMPLE 41

(2RS,5RS)-N-{3-[5-(4-Fluoro-phenyl)-1-(toluene-4-sulfonyl)-pyrrolidin-2-yl]-propyl}-propionamide Acylation of (2RS,5RS)-[5-(4-fluoro-phenyl)-1-(toluene-4-sulfonyl)-pyrrolidin-2-yl]-propylamine according to the general method of example 6c yielded the title compound as a colorless oil, MS: m/e=433.4 (M+H$^+$).

EXAMPLE 42

(2RS,5RS)-N-{3-[5-(4-Fluoro-phenyl)-1-(toluene-4-sulfonyl)-pyrrolidin-2-yl]-propyl}-2,2-dimethyl-propionamide Acylation of (2RS,5RS)-[5-(4-fluoro-phenyl)-1-(toluene-4-sulfonyl)-pyrrolidin-2-yl]-propylamine according to the general method of example 6c yielded the title compound as a colorless oil, MS: m/e=461.3 (M+H$^+$).

EXAMPLE 43

(2RS,5RS)-Cyclopentanecarboxylic acid {3-[5-(4-fluoro-phenyl)-1-(toluene-4-sulfonyl)-pyrrolidin-2-yl]-propyl}-amide Acylation of (2RS,5RS)-[5-(4-fluoro-phenyl)-1-(toluene-4-sulfonyl)-pyrrolidin-2-yl]-propylamine according to the general method of example 6c yielded the title compound as a colorless oil, MS: m/e=473.3 (M+H$^+$).

EXAMPLE 44

(2RS,5RS)-3-[5-(4-Fluoro-phenyl)-1-(toluene-4-sulfonyl)-pyrrolidin-2-yl]-propan-1-ol Reduction of (2RS,5SR)-3-[5-(4-fluoro-phenyl)-1-(toluene-4-sulfonyl)-pyrrolidin-2-yl]-propionic acid methyl ester with lithium aluminum hydride (1.5 eq.) in THF at RT, aqueous work-up and crystallization from EE/hexane yielded the title compound, white solid, m.p. 93° C. and MS: m/e=378.2 (M+H$^+$).

EXAMPLE 45

(2RS,5RS)-4-[5-(4-Fluoro-phenyl)-1-(toluene-4-sulfonyl)-pyrrolidin-2-yl]-butyronitrile Transformation of (2RS,5RS)-3-[5-(4-Fluoro-phenyl)-1-(toluene-4-sulfonyl)-pyrrolidin-2-yl]-propan-1-ol according to the general method of example 10 yielded the title compound, off-white solid, m.p. 74° C. and MS: m/e=386 (M+).

EXAMPLE 46

(2RS,5RS)-N-{4-[5-(4-Fluoro-phenyl)-1-(toluene-4-sulfonyl)-pyrrolidin-2-yl]-butyl}-acetamide Hydrogenation of (2RS,5RS)-[5-(4-fluoro-phenyl)-1-(toluene-4-sulfonyl)-pyrrolidin-2-yl]-butyronitrile according to the general method of example 9a and subsequent acetylation of the corresponding (2RS,5RS)-[5-(4-fluoro-phenyl)-1-(toluene-4-sulfonyl)-pyrrolidin-2-yl]-butylamine in accordance with the general method of example 6c yielded the title compound as a colorless oil, MS: m/e=433.4 (M+H+).

EXAMPLE 47

(2RS,5RS)-Cyclopropanecarboxylic acid {4-[5-(4-fluoro-phenyl)-1-(toluene-4-sulfonyl)-pyrrolidin-2-yl]-butyl}-amide Acylation of (2RS,5RS)-[5-(4-fluoro-phenyl)-1-(toluene-4-sulfonyl)-pyrrolidin-2-yl]-butylamine according to the general method of example 6c yielded the title compound as a colorless oil, MS: m/e=459.5 (M+H+).

EXAMPLE 48

(2RS,5RS)-5-[5-(4-Fluoro-phenyl)-1-(toluene-4-sulfonyl)-pyrrolidin-2-yl]-pentanoic acid amide Transformation of (2RS,5SR)-3-[5-(4-fluoro-phenyl)-1-(toluene-4-sulfonyl)-pyrrolidin-2-yl]-propan-1-ol in accordance with the general method of example 29a–c gave the title compound as an off-white semisolid, MS: m/e=419.3 (M+H+).

EXAMPLE 49

(2RS,5RS)-5-{3-[5-(4-Fluoro-phenyl)-1-(toluene-4-sulfonyl)-pyrrolidin-2-yl]-propyl}-2-methyl-2H-tetrazole The title compound, light yellow solid, m.p. 107° C. and MS: m/e=444.3 (M+H+) was prepared in accordance with the general method of example 27a/b from (2RS,5RS)-[5-(4-fluoro-phenyl)-1-(toluene-4-sulfonyl)-pyrrolidin-2-yl]-butyronitrile.

EXAMPLE 50

(2RS,5RS)-5-{3-[5-(4-Fluoro-phenyl)-1-(toluene-4-sulfonyl)-pyrrolidin-2-yl]-propyl}-1-methyl-1H-tetrazole The title compound, white solid, m.p. 153° C. and MS: m/e=444.3 (M+H+) was prepared in accordance with the general method of example 27a/b from (2RS,5RS)-[5-(4-fluoro-phenyl)-1-(toluene-4-sulfonyl)-pyrrolidin-2-yl]-butyronitrile.

EXAMPLE 51

(2RS,5RS)-5-[5-(4-Fluoro-phenyl)-1-(toluene-4-sulfonyl)-pyrrolidin-2-yl]-pentanenitrile The title compound, white solid, m.p. 79° C. and MS: m/e=401.2 (M+H+) was prepared in accordance with the general method of example 4 from (2RS,5RS)-3-[5-(4-fluoro-phenyl)-1-(toluene-4-sulfonyl)-pyrrolidin-2-yl]-pentanoic acid amide.

EXAMPLE 52

(2RS,5RS)-4-[5-(4-Fluoro-phenyl)-1-(toluene-4-sulfonyl)-pyrrolidin-2-yl]-N-hydroxy-butyramidine The title compound, white foam, MS: m/e=420.3 (M+H+) was prepared in accordance with the general method of example 7 from (2RS,5RS)-[5-(4-fluoro-phenyl)-1-(toluene-4-sulfonyl)-pyrrolidin-2-yl]-butyronitrile.

EXAMPLE 53

(2RS,5RS)-N-{5-[5-(4-Fluoro-phenyl)-1-(toluene-4-sulfonyl)-pyrrolidin-2-yl]-pentyl}-acetamide Hydrogenation of (2RS,5RS)-[5-(4-fluoro-phenyl)-1-(toluene-4-sulfonyl)-pyrrolidin-2-yl]-pentanenitrile according to the general method of example 9a and subsequent acetylation of the corresponding (2RS,5RS)-[5-(4-fluoro-phenyl)-1-(toluene-4-sulfonyl)-pyrrolidin-2-yl]-pentylamine in accordance with the general method of example 6c yielded the title compound as a colorless oil, MS: m/e=447.4 (M+H+).

EXAMPLE 54

(2RS,5RS)-5-{4-[5-(4-Fluoro-phenyl)-1-(toluene-4-sulfonyl)-pyrrolidin-2-yl]-butyl}-1-methyl-1H-tetrazole The title compound, white solid, m.p. 120° C. and MS: m/e=458.4 (M+H+) was prepared in accordance with the general method of example 27a/b from (2RS,5RS)-[5-(4-fluoro-phenyl)-1-(toluene-4-sulfonyl)-pyrrolidin-2-yl]-pentanenitrile.

A second product of this reaction was (2RS,5RS)-5-{4-[5-(4-fluoro-phenyl)-1-(toluene-4-sulfonyl)-pyrrolidin-2-yl]-butyl}-2-methyl-2H-tetrazole, light yellow solid, m.p. 77° C. and MS: m/e=458.4 (M+H+).

EXAMPLE 55

(2RS,5RS)-5-[5-(4-Fluoro-phenyl)-1-(toluene-4-sulfonyl)-pyrrolidin-2-yl]-N-hydroxy-pentanamidine The title compound, white foam, MS: m/e=434.5 (M+H+) was prepared in accordance with the general method of example 7 from (2RS,5RS)-[5-(4-fluoro-phenyl)-1-(toluene-4-sulfonyl)-pyrrolidin-2-yl]-pentanenitrile.

EXAMPLE 56

(2RS,5SR)-N-{2-[1-(4-Chloro-benzenesulfonyl)-5-(4-fluoro-phenyl)-pyrrolidin-2-yl]-ethyl}-acetamide a) (2RS,5SR)-1-(4-chloro-benzenesulfonyl)-5-(4-fluoro-phenyl)-pyrrolidine-2-carboxylic acid methyl ester Reaction of (2RS,5SR)-5-(4-fluoro-phenyl)-pyrrolidine-2-carboxylate with 4-chloro-benzenesulfonyl chloride according to the general procedure 1d yielded (2RS,5SR)-1-(4-chloro-benzenesulfonyl)-5-(4-fluoro-phenyl)-pyrrolidine-2-carboxylic acid methyl ester as an off-white solid, MS: m/e=398 (M$^+$).

b) (2RS,5SR)-[1-(4-chloro-benzenesulfonyl)-5-(4-fluoro-phenyl)-pyrrolidine-2-yl]-methanol Reduction of (2RS,5SR)-1-(4-chloro-benzenesulfonyl)-5-(4-fluoro-phenyl)-pyrrolidine-2-carboxylic acid methyl ester with LiAlH$_4$ according to the general method of example 2 gave (2RS,5SR)-[1-(4-chloro-benzenesulfonyl)-5-(4-fluoro-phenyl)-pyrrolidine-2-yl]-methanol as a colorless oil, MS: m/e=370 (M$^+$).

c) (2RS,5SR)-[1-(4-chloro-benzenesulfonyl)-5-(4-fluoro-phenyl)-pyrrolidine-2-yl]-acetonitrile Transformation of (2RS,5SR)-[1-(4-chloro-benzenesulfonyl)-5-(4-fluoro-phenyl)-pyrrolidine-2-yl]-methanol according to the general procedure of example 10 yielded (2RS,5SR)-[1-(4-chloro-benzenesulfonyl)-5-(4-fluoro-phenyl)-pyrrolidine-2-yl]-acetonitrile as a light yellow oil, MS: m/e=379 (M$^+$).

d) (2RS,5SR)-N-{2-[1-(4-Chloro-benzenesulfonyl)-5-(4-fluoro-phenyl)-pyrrolidin-2-yl]-ethyl}-acetamide Hydrogenation of (2RS,5SR)-[1-(4-chloro-benzenesulfonyl)-5-(4-fluoro-phenyl)-pyrrolidine-2-yl]-acetonitrile according to the general method of example 9a and subsequent acetylation of the corresponding (2RS,5SR)-[1-(4-chloro-benzenesulfonyl)-5-(4-fluoro-phenyl)-pyrrolidine-2-yl]-ethylamine in accordance with the general method of example 6c yielded the title compound as a white solid, m.p 103° C. and MS: m/e=425.3 (M+H$^+$).

EXAMPLE 57

(2RS,5SR)-Cyclopropanecarboxylic acid {2-[1-(4-chloro-benzenesulfonyl)-5-(4-fluoro-phenyl)-pyrrolidin-2-yl]-ethyl}-amide Acylation of (2RS,5SR)-[1-(4-chloro-benzenesulfonyl)-5-(4-fluoro-phenyl)-pyrrolidine-2-yl]-ethylamine according to the general method of example 6c yielded the title compound as a white solid, m.p. 80° C. and MS: m/e=451.3 (M+H$^+$).

EXAMPLE 58

(2R,5S)-[5-(4-Fluoro-phenyl)-1-(toluene-4-sulfonyl)-pyrrolidin-2-yl]-methanol a) (2R,5S)-5-(4-fluoro-phenyl)-1-(toluene-4-sulfonyl)-pyrrolidine-2-carboxylic acid ethyl ester Reaction of ethyl (2R,5S)-5-(4-fluoro-phenyl)-pyrrolidine-2-carboxylate [prepared from (S)-ethyl N-Boc-pyroglutamate and (4-fluoro-phenyl)magnesium bromide according to: a) Tetrahedron Letters 34 (1993) 6317–6320. b) Journal of Medicinal Chemistry 39 (1996) 2594–2608. and c) Tetrahedron: Asymmetry 10 (1999) 2245–2303.] and toluene-4-sulfonyl chloride according to the general method of example 1d yielded (2R,5S)-5-(4-fluoro-phenyl)-1-(toluene-4-sulfonyl)-pyrrolidine-2-carboxylic acid ethyl ester as a white solid, m.p. 78° C., $[\alpha]_D^{20}$=−36.9° (c=1.0151 in chloroform) and MS: m/e=392.2 (M+H$^+$).

The (2S,5R)-5-(4-fluoro-phenyl)-1-(toluene-4-sulfonyl)-pyrrolidine-2-carboxylic acid ethyl ester [white solid, m.p. 78° C., $[\alpha]_D^{20}$=+34.7° (c=1.0709 in chloroform) and MS: m/e=392.2 (M+H$^+$)] was prepared from ethyl (2S,5R)-5-(4-fluoro-phenyl)-pyrrolidine-2-carboxylate.

b) (2R,5S)-[5-(4-Fluoro-phenyl)-1-(toluene-4-sulfonyl)-pyrrolidin-2-yl]-methanol Reduction of (2R,5S)-5-(4-fluoro-phenyl)-1-(toluene-4-sulfonyl)-pyrrolidine-2-carboxylic acid ethyl ester according to the general method of example 2 gave the title compound as a white solid, m.p. 140° C., $[\alpha]_D^{20}$=−135.3° (c=1.0642 in chloroform) and MS: m/e=350.2 (M+H$^+$).

(2S,5R)-[5-(4-Fluoro-phenyl)-1-(toluene-4-sulfonyl)-pyrrolidin-2-yl]-methanol: white solid, m.p. 140° C., $[\alpha]_D^{20}$=+135.9° (c=1.0789 in chloroform) and MS: m/e=350.1 (M+H$^+$).

EXAMPLE 59

(2R,5S)-3-[5-(4-Fluoro-phenyl)-1-(toluene-4-sulfonyl)-pyrrolidin-2-yl]-propionamide The title compound, light yellow foam, $[\alpha]_D^{20}$=−124.4° (c=1.0865 in chloroform) and MS: m/e=391.1 (M+H$^+$), was prepared in accordance with the general method of example 29 from (2R,5S)-[5-(4-fluoro-phenyl)-1-(toluene-4-sulfonyl)-pyrrolidin-2-yl]-methanol.

(2S,5R)-3-[5-(4-Fluoro-phenyl)-1-(toluene-4-sulfonyl)-pyrrolidin-2-yl]-propionamide: light yellow foam, $[\alpha]_D^{20}$=+124.2° (c=1.1010 in chloroform) and MS: m/e=391.2 (M+H$^+$).

EXAMPLE 60

(2S,5S)-N-{3-[5-(4-Fluoro-phenyl)-1-(toluene-4-sulfonyl)-pyrrolidin-2-yl]-propyl}-acetamide a) (2R,5S)-3-[5-(4-fluoro-phenyl)-1-(toluene-4-sulfonyl)-pyrrolidin-2-yl]-propionitrile Reaction of (2R,5S)-3-[5-(4-fluoro-phenyl)-1-(toluene-4-sulfonyl)-pyrrolidin-2-yl]-propionamide in accordance with the general method of example 4 yielded (2R,5S)-3-[5-(4-fluoro-phenyl)-1-(toluene-4-sulfonyl)-pyrrolidin-2-yl]-propionitrile as a light brown oil, $[\alpha]_D^{20}$=−95.0° (c=1.0972 in chloroform) and MS: m/e=372 (M$^+$).

(2S,5R)-3-[5-(4-Fluoro-phenyl)-1-(toluene-4-sulfonyl)-pyrrolidin-2-yl]-propionitrile: light brown oil, $[\alpha]_D^{20}$=+94.4° (c=1.0955 in chloroform) and MS: m/e=372 (M$^+$).

b) (2S,5S)-N-{3-[5-(4-Fluoro-phenyl)-1-(toluene-4-sulfonyl)-pyrrolidin-2-yl]-propyl}-acetamide The title compound, colorless semisolid, $[\alpha]_D^{20}$=−70.7° (c=1.1206 in chloroform) and MS: m/e=419.3 (M+H$^+$) was prepared as described for the racemic compound (example 32) from (2R,5S)-3-[5-(4-fluoro-phenyl)-1-(toluene-4-sulfonyl)-pyrrolidin-2-yl]-propionitrile.

(2R,5R)-N-{3-[5-(4-Fluoro-phenyl)-1-(toluene-4-sulfonyl)-pyrrolidin-2-yl]-propyl}-acetamide: colorless semisolid, $[\alpha]_D^{20}$=+71.6° (c=1.1446 in chloroform) and MS: m/e=419.3 (M+H$^+$).

EXAMPLE 61

(2S,5S)-Cyclopropanecarboxylic acid {3-[5-(4-fluoro-phenyl)-1-(toluene-4-sulfonyl)-pyrrolidin-2-yl]-propyl}-amide The title compound, crystallized from oil, white, $[\alpha]_D^{20}$=−61.7° (c=1.0926 in chloroform) and MS: m/e=445.4 (M+H$^+$) was prepared as described for the racemic compound (example 33) from (2R,5S)-3-[5-(4-fluoro-phenyl)-1-(toluene-4-sulfonyl)-pyrrolidin-2-yl]-propionitrile.

(2R,5R)-Cyclopropanecarboxylic acid {3-[5-(4-fluoro-phenyl)-1-(toluene-4-sulfonyl)-pyrrolidin-2-yl]-propyl}-amide: crystallized from oil, white, $[\alpha]_D^{20}$=+60.2° (c=1.0764 in chloroform) and MS: m/e=445.3 (M+H$^+$).

EXAMPLE 62

(2R,5S)-5-{2-[5-(4-Fluoro-phenyl)-1-(toluene-4-sulfonyl)-pyrrolidin-2-yl]-ethyl}-2-methyl-2H-tetrazole The title compound, crystallized from oil, white, $[\alpha]_D^{20}$=−58.6° (c=1.0632 in chloroform) and MS: m/e=430.2 (M+H$^+$) was prepared in accordance with the general method of example 27 from (2R,5S)-3-[5-(4-fluoro-phenyl)-1-(toluene-4-sulfonyl)-pyrrolidin-2-yl]-propionitrile.

(2S,5R)-5-{2-[5-(4-Fluoro-phenyl)-1-(toluene-4-sulfonyl)-pyrrolidin-2-yl]-ethyl}-2-methyl-2H-tetrazole: crystallized from oil, white, $[\alpha]_D^{20}$=+59.3° (c=1.0812 in chloroform) and MS: m/e=430.3 (M+H$^+$).

EXAMPLE 63

(2R,5S)-5-{2-[5-(4-Fluoro-phenyl)-1-(toluene-4-sulfonyl)-pyrrolidin-2-yl]-ethyl}-1-methyl-1H-tetrazole The title compound, crystallized from oil, light yellow, $[\alpha]_D^{20}$=−97.6° (c=1.0795 in chloroform) and MS: m/e=430.2 (M+H$^+$) was prepared in accordance with the general method of example 27 from (2R,5S)-3-[5-(4-fluoro-phenyl)-1-(toluene-4-sulfonyl)-pyrrolidin-2-yl]-propionitrile (see example 62, regioisomer).

(2S,5R)-5-{2-[5-(4-Fluoro-phenyl)-1-(toluene-4-sulfonyl)-pyrrolidin-2-yl]-ethyl}-1-methyl-1H-tetrazole: crystallized from oil, light yellow, $[\alpha]_D^{20}$=+100.7° (c=1.0749 in chloroform) and MS: m/e=430.1 (M+H$^+$).

EXAMPLE 64

(2S,5S)-3-[5-(4-Fluoro-phenyl)-1-(toluene-4-sulfonyl)-pyrrolidin-2-yl]-propan-1-ol The title compound, white solid, m.p. 96° C., $[\alpha]_D^{20}$=−97.1° (c=1.0723 in chloroform) and MS: m/e=378.2 (M+H$^+$)] was prepared in accordance with the general method of example 44 from (2S,5R)-3-[5-(4-fluoro-phenyl)-1-(toluene-4-sulfonyl)-pyrrolidin-2-yl]-propionic acid methyl ester [see example 59: colorless oil, $[\alpha]_D^{20}$=−96.4° (c=1.0992 in chloroform) and MS: m/e=406.1 (M+H$^+$)].

(2R,5R)-3-[5-(4-Fluoro-phenyl)-1-(toluene-4-sulfonyl)-pyrrolidin-2-yl]-propan-1-ol: white solid, m.p. 96° C., $[\alpha]_D^{20}$=+97.5° (c=1.1287 in chloroform) and MS: m/e=378.2 (M+H$^+$); [(2R,5S)-3-[5-(4-fluoro-phenyl)-1-(toluene-4-sulfonyl)-pyrrolidin-2-yl]-propionic acid methyl ester: colorless oil, $[\alpha]_D^{20}$=+94.0° (c=1.0868 in chloroform) and MS: m/e=406.1 (M+H$^+$)].

EXAMPLE 65

(2RS,5SR)-3-[1-(4-Chloro-benzenesulfonyl)-5-(4-fluoro-phenyl)-pyrrolidin-2-yl]-propionamide a) (2RS,5SR)-3-[1-(4-chloro-benzenesulfonyl)-5-(4-fluoro-phenyl)-pyrrolidin-2-yl]-propionic acid methyl ester Reaction of (2RS,5SR)-[1-(4-chloro-benzenesulfonyl)-5-(4-fluoro-phenyl)-pyrrolidine-2-yl]-methanol in accordance with general method of example 29a/b yielded (2RS,5SR)-3-[1-(4-chloro-benzenesulfonyl)-5-(4-fluoro-phenyl)-pyrrolidin-2-yl]-propionic acid methyl ester as a colorless oil, MS: m/e=426.1 (M+H$^+$).

b) (2RS,5SR)-3-[1-(4-Chloro-benzenesulfonyl)-5-(4-fluoro-phenyl)-pyrrolidin-2-yl]-propionamide The title compound, light brown solid, m.p. 114° C. and MS: m/e=411 (M$^+$) was prepared in accordance with the general method of example 3 from (2RS,5SR)-3-[1-(4-chloro-benzenesulfonyl)-5-(4-fluoro-phenyl)-pyrrolidin-2-yl]-propionic acid methyl ester.

EXAMPLE 66

(2RS,5RS)-N-{3-[1-(4-Chloro-benzenesulfonyl)-5-(4-fluoro-phenyl)-pyrrolidin-2-yl]-propyl}-acetamide a) (2RS,5SR)-3-[1-(4-chloro-benzenesulfonyl)-5-(4-fluoro-phenyl)-pyrrolidin-2-yl]-propionitrile Reaction of (2RS,5SR)-3-[1-(4-chloro-benzenesulfonyl)-5-(4-fluoro-phenyl)-pyrrolidin-2-yl]-propionamide according to general method of example 4 gave (2RS,5SR)-3-[1-(4-chloro-benzenesulfonyl)-5-(4-fluoro-phenyl)-pyrrolidin-2-yl]-propionitrile as a white solid, m.p. 108° C. and MS: m/e=393 (M$^+$).

b) (2RS,5RS)-N-{3-[1-(4-Chloro-benzenesulfonyl)-5-(4-fluoro-phenyl)-pyrrolidin-2-yl]-propyl}-acetamide Hydrogenation of (2RS,5SR)-[1-(4-chloro-benzenesulfonyl)-5-(4-fluoro-phenyl)-pyrrolidine-2-yl]-propionitrile according to the general method of example 9a and subsequent acetylation of the corresponding (2RS,5SR)-[1-(4-chloro-benzenesulfonyl)-5-(4-fluoro-phenyl)-pyrrolidine-2-yl]-propylamine in accordance with the general method of example 6c yielded the title compound as a white solid, m.p. 49° C. and MS: m/e=439.3 (M+H$^+$).

EXAMPLE 67

(2RS,5SR)-3-[1-(4-Chloro-benzenesulfonyl)-5-(4-fluoro-phenyl)-pyrrolidin-2-yl]-propan-1-ol Reduction of (2RS,5SR)-3-[1-(4-chloro-benzenesulfonyl)-5-(4-fluoro-phenyl)-pyrrolidin-2-yl]-propionic acid methyl ester in accordance with general method of example 2 yielded the title compound as a colorless oil, MS: m/e=498 (M$^+$).

EXAMPLE 68

(2RS,5RS)-4-[5-(4-Fluoro-phenyl)-1-(toluene-4-sulfonyl)-pyrrolidin-2-yl]-butyramide A mixture of (2RS,5RS)-4-[5-(4-fluoro-phenyl)-1-(toluene-4-sulfonyl)-pyrrolidin-2-yl]-butyronitrile (2.0 g, 5.17 mmol) and conc. sulfuric acid (20 ml) was stirred at RT for 17 h, poured into 150 ml ice/water and extracted with ethyl acetate (2×100 ml). The combined organic layers were washed with water (100 ml), dried (MgSO$_4$) and evaporated to give the title compound as a white foam, MS: m/e=404 (M$^+$).

EXAMPLE 69

(2RS,5RS)-5-{3-[5-(4-Fluoro-phenyl)-1-(toluene-4-sulfonyl)-pyrrolidin-2-yl]-propyl}-1-methyl-1H-[1,2,4]triazole The title compound, colorless oil, MS: m/e=443.2 (M+H$^+$), was prepared in accordance with the general method of example 26 from (2RS,5RS)-4-[5-(4-fluoro-phenyl)-1-(toluene-4-sulfonyl)-pyrrolidin-2-yl]-butyronitrile and methylhydrazine.

EXAMPLE 70

(2RS,5RS)-3-{3-[5-(4-Fluoro-phenyl)-1-(toluene-4-sulfonyl)-pyrrolidin-2-yl]-propyl}-1-methyl-1H-[1,2,4]triazole The title compound, colorless oil, MS: m/e=443.2 (M+H$^+$), was prepared in accordance with the general method of example 26 from (2RS,5RS)-4-[5-(4-fluoro-phenyl)-1-(toluene-4-sulfonyl)-pyrrolidin-2-yl]-butyronitrile and methylhydrazine.

EXAMPLE 71

(2RS,5RS)-5-{3-[5-(4-Fluoro-phenyl)-1-(toluene-4-sulfonyl)-pyrrolidin-2-yl]-propyl}-3-methyl-[1,2,4]oxadiazole a) (2RS,5RS)-4-[5-(4-fluoro-phenyl)-1-(toluene-4-sulfonyl)-pyrrolidin-2-yl]-butyric acid A stirred mixture of (2RS,5RS)-4-[5-(4-fluoro-phenyl)-1-(toluene-4-sulfonyl)-pyrrolidin-2-yl]-butyramide (1.57 g, 3.88 mmol) and conc. hydrochloric acid (30 ml) was heated under reflux conditions for 3 h, poured into ice/water (150 ml) and extracted with ethyl acetate (2×100 ml). The combined organic layers were washed with brine (2×80 ml), dried (MgSO$_4$) and evaporated. The crude product was purified by crystallization from ethyl acetate/hexane to give (2RS,5RS)-4-[5-(4-fluoro-phenyl)-1-(toluene-4-sulfonyl)-pyrrolidin-2-yl]-butyric acid (1.45 g, yield 92%) as an off-white solid, m.p. 87° C. and MS: m/e=404.4 (M–H$^+$).

b) (2RS,5RS)-5-{3-[5-(4-Fluoro-phenyl)-1-(toluene-4-sulfonyl)-pyrrolidin-2-yl]-propyl}-3-methyl-[1,2,4]oxadiazole The title compound, white solid, m.p. 91° C. and MS: m/e=443 (M$^+$) was prepared in accordance with the general method of example 13 from N-hydroxy-acetamidine and (2RS,5RS)-3-[5-(4-fluoro-phenyl)-1-(toluene-4-sulfonyl)-pyrrolidin-2-yl]-butyric acid.

EXAMPLE 72

(2RS,5RS)-3-{3-[5-(4-Fluoro-phenyl)-1-(toluene-4-sulfonyl)-pyrrolidin-2-yl]-propyl}-[1,2,4]oxadiazole The title compound, colorless oil, MS: m/e=430.3 (M+H$^+$) was prepared in accordance with the general method of example 14 from (2RS,5RS)-2-[5-(4-fluoro-phenyl)-1-(toluene-4-sulfonyl)-pyrrolidin-2-yl]-N-hydroxy-butyramidine.

EXAMPLE 73

(2RS,5SR)-5-{2-[1-(4-Chloro-benzenesulfonyl)-5-(4-fluoro-phenyl)-pyrrolidin-2-yl]-ethyl}-2-methyl-2H-tetrazole The title compound, colorless gum, MS: m/e=450.2 (M+H$^+$) was prepared in accordance with the general method of example 27a/b from (2RS,5RS)-[5-(4-fluoro-phenyl)-1-(4-chloro-benzenesulfonyl)-pyrrolidin-2-yl]-propionitrile.

A second product of this reaction was (2RS,5RS)-5-{4-[5-(4-fluoro-phenyl)-1-(4-chloro-benzenesulfonyl)-pyrrolidin-2-yl]-butyl}-2-methyl-2H-tetrazole, white solid, m.p. 122° C. and MS: m/e=450.2 (M+H$^+$).

EXAMPLE 74

(2RS,5SR)-2-(4-Fluoro-phenyl)-5-(2-methoxy-ethyl)-1-(toluene-4-sulfonyl)-pyrrolidine Methylation of (2RS,5RS)-3-[5-(4-fluoro-phenyl)-1-(toluene-4-sulfonyl)-pyrrolidin-2-yl]-ethan-1-ol according to the general method of example 8 yielded the title compound as colorless oil, MS: m/e=378.2 (M+H$^+$).

EXAMPLE 75

(2RS,5SR)-3-Cyclopropyl-5-{2-[5-(4-fluoro-phenyl)-1-(toluene-4-sulfonyl)-pyrrolidin-2-yl]-ethyl}-[1,2,4]oxadiazole The title compound, white solid, m.p. 129° C. and MS: m/e=456.4 (M$^+$) was prepared in accordance with the general method of example 13 from N-hydroxy-cyclopropane-carboxamidine and (2RS,5SR)-3-[5-(4-fluoro-phenyl)-1-(toluene-4-sulfonyl)-pyrrolidin-2-yl]-propionic acid.

EXAMPLE 76

(2RS,5RS)-N-{3-[5-(4-Fluoro-phenyl)-1-(toluene-4-sulfonyl)-pyrrolidin-2-yl]-propyl}-benzamide Acylation of (2RS,5RS)-[5-(4-fluoro-phenyl)-1-(toluene-4-sulfonyl)-pyrrolidin-2-yl]-propylamine according to the general method of example 6c yielded the title compound as a colorless oil, MS: m/e=481.4 (M+H$^+$).

EXAMPLE 77

(2RS,5RS)-N-{3-[5-(4-Fluoro-phenyl)-1-(toluene-4-sulfonyl)-pyrrolidin-2-yl]-propyl}-methanesulfonamide Reaction of (2RS,5RS)-[5-(4-fluoro-phenyl)-1-(toluene-4-sulfonyl)-pyrrolidin-2-yl]-propylamine with methanesulfonyl chloride according to the general method of example 1d yielded the title compound as a white solid, m.p. 123° C. and MS: m/e=455.3 (M+H$^+$).

EXAMPLE 78

(2RS,5SR)-5-{2-[5-(4-Fluoro-phenyl)-1-(toluene-4-sulfonyl)-pyrrolidin-2-yl]-ethyl}-1-methyl-1H-[1,2,4]triazole The title compound, white solid, m.p.=145° C. and MS: m/e=429.5 (M+H$^+$), was prepared in accordance with the general method of example 26 from (2RS,5RS)-4-[5-(4-fluoro-phenyl)-1-(toluene-4-sulfonyl)-pyrrolidin-2-yl]-propionitrile and methylhydrazine.

EXAMPLE 79

(2RS,5SR)-3-{2-[5-(4-Fluoro-phenyl)-1-(toluene-4-sulfonyl)-pyrrolidin-2-yl]-ethyl}-1-methyl-1H-[1,2,4]triazole The title compound, colorless oil, MS: m/e=429.5 (M+H$^+$), was prepared in accordance with the general method of example 26 from (2RS,5RS)-4-[5-(4-fluoro-phenyl)-1-(toluene-4-sulfonyl)-pyrrolidin-2-yl]-propionitrile and methylhydrazine.

EXAMPLE 80

(2RS,5RS)-2,2,2-Trifluoro-N-{3-[5-(4-fluoro-phenyl)-1-(toluene-4-sulfonyl)-pyrrolidin-2-yl]-propyl}-acetamide Acylation of (2RS,5RS)-[5-(4-fluoro-phenyl)-1-(toluene-4-sulfonyl)-pyrrolidin-2-yl]-propylamine according to the general method of example 6c yielded the title compound as a colorless oil, MS: m/e=473.1 (M+H$^+$).

EXAMPLE 81

(2RS,5RS)-1-{3-[5-(4-Fluoro-phenyl)-1-(toluene-4-sulfonyl)-pyrrolidin-2-yl]-propyl}-3-methyl-thiourea Reaction of (2RS,5RS)-[5-(4-fluoro-phenyl)-1-(toluene-4-sulfonyl)-pyrrolidin-2-yl]-propylamine (0.5 g, 1.33 mmol) with methyl isothiocyanate (117 mg, 1.59 mmol) in dichloromethane (10 ml) at RT and purification of the crude product by column chromatography on silica gel (ethyl acetate) yielded the title compound (0.48 g, yield 80%) as a white foam, MS: m/e=450.4 (M+H$^+$).

EXAMPLE 82

(2RS,5RS)-1-{3-[5-(4-Fluoro-phenyl)-1-(toluene-4-sulfonyl)-pyrrolidin-2-yl]-propyl}-1H-[1,2,4]triazole a) (2RS,5RS)-2-(3-chloro-propyl)-5-(4-fluoro-phenyl)-1-(toluene-4-sulfonyl)-pyrrolidine Reaction of (2RS,5RS)-3-[5-(4-fluoro-phenyl)-1-(toluene-4-sulfonyl)-pyrrolidin-2-yl]-propan-1-ol according to the general method of example 5 yielded (2RS,5RS)-2-(3-chloro-propyl)-5-(4-fluoro-phenyl)-1-(toluene-4-sulfonyl)-pyrrolidine as a light brow solid,
m.p.=81° C. and MS: m/e=396.3 (M+H$^+$).

b) (2RS,5RS)-1-{3-[5-(4-Fluoro-phenyl)-1-(toluene-4-sulfonyl)-pyrrolidin-2-yl]-propyl}-1H-[1,2,4]triazole To a stirred solution of 1,2,4-triazol (105 mg, 1.52 mmol) in DMF (15 ml) was added at 0° C. sodium hydride (61 mg, 1.52 mmol; 60%-disp.). The mixture was stirred at RT for 1 h, cooled to 0° C. and (2RS,5RS)-2-(3-chloro-propyl)-5-(4-fluoro-phenyl)-1-(toluene-4-sulfonyl)-pyrrolidine (0.50 g, 1.26 mmol) was added. The reaction mixture was stirred at RT for 3 h and at 50° C. for 16 h, poured into ice/water (70 ml) and extracted with dichloromethane (2×100 ml). The combined organic layers were washed with water (70 ml) and brine (70 ml), dried (MgSO$_4$) and evaporated. The crude product was purified by column chromatography on silica gel (ethyl acetate) to yield the title compound (0.47 g, yield 87%) as a colorless oil, MS: m/e=429.5 (M+H$^+$).

EXAMPLE 83

(2RS,5RS)-2-(4-Fluoro-phenyl)-5-(3-methoxy-propyl)-1-(toluene-4-sulfonyl)-pyrrolidine Methylation of (2RS,5RS)-3-[5-(4-fluoro-phenyl)-1-(toluene-4-sulfonyl)-pyrrolidin-2-yl]-propan-1-ol according to the general method of example 8 yielded the title compound as light yellow oil, MS: m/e=392.2 (M+H$^+$).

EXAMPLE 84

(RS)-N-{3-[1-(Toluene-4-sulfonyl)-pyrrolidin-2-yl]-propyl}-acetamide a) (RS)-1-(toluene-4-sulfonyl)-pyrrolidine-2-carboxylic acid methyl ester Reaction of DL-proline methylester with toluene-4-sulfonyl chloride according to the general procedure of example 1d yielded (RS)-1-(toluene-4-sulfonyl)-pyrrolidine-2-carboxylic acid methyl ester as a white solid, m.p.=93° C. and MS: m/e=283 (M$^+$).

b) (RS)-[1-(toluene-4-sulfonyl)-pyrrolidine-2-yl]-methanol

Reduction of (RS)-1-(toluene-4-sulfonyl)-pyrrolidine-2-carboxylic acid methyl ester with LiAlH$_4$ according to the general method of example 2 gave (RS)-[1-(toluene-4-sulfonyl)-pyrrolidine-2-yl]-methanol as a colorless oil, MS: m/e=255 (M$^+$).

c) (RS)-3-[1-(toluene-4-sulfonyl)-pyrrolidin-2-yl]-propionic acid methyl ester

Reaction of (RS)-[1-(toluene-4-sulfonyl)-pyrrolidine-2-yl]-methanol in accordance with general method of example 29a/b yielded (RS)-3-[1-(toluene-4-sulfonyl)-pyrrolidin-2-yl]-propionic acid methyl ester as an off-white semisolid, MS: m/e=312.1 (M+H$^+$).

d) (RS)-3-[1-(Toluene-4-sulfonyl)-pyrrolidin-2-yl]-propionamide (RS)-3-[1-(Toluene-4-sulfonyl)-pyrrolidin-2-yl]-propionamide, light brown oil, MS: m/e=297.1 (M+H$^+$) was prepared in accordance with the general method of example 3 from (RS)-3-[1-(toluene-4-sulfonyl)-pyrrolidin-2-yl]-propionic acid methyl ester.

e) (RS)-3-[1-(toluene-4-sulfonyl)-pyrrolidin-2-yl]-propionitrile

Reaction of (RS)-3-[1-(toluene-4-sulfonyl)-pyrrolidin-2-yl]-propionamide according to general method of example 4 gave (RS)-3-[1-(toluene-4-sulfonyl)-pyrrolidin-2-yl]-propionitrile as a white semisolid, MS: m/e=278 (M$^+$).

37 f) (RS)-N-{3-[1-(Toluene-4-sulfonyl)-pyrrolidin-2-yl]-propyl}-acetamide

Hydrogenation of (RS)-[1-(toluene-4-sulfonyl)-pyrrolidine-2-yl]-propionitrile according to the general method of example 9a and subsequent acetylation of the corresponding (RS)-[1-(toluene-4-sulfonyl)-pyrrolidine-2-yl]-propylamine in accordance with the general method of example 6c yielded the title compound as a colorless oil, MS: m/e=325.4 (M+H$^+$).

EXAMPLE 85

(2RS,5RS)-1-{3-[5-(4-Fluoro-phenyl)-1-(toluene-4-sulfonyl)-pyrrolidin-2-yl]-propyl}-1H-imidazole The title compound, colorless oil, MS: m/e=428.5 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 1H-imidazole.

EXAMPLE 86

(2RS,5RS)-1-{3-[5-(4-Fluoro-phenyl)-1-(toluene-4-sulfonyl)-pyrrolidin-2-yl]-propyl}-1H-pyrazole The title compound, colorless oil, MS: m/e=428.5 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 1H-pyrazole.

EXAMPLE 87

(RS)-Cyclopropanecarboxylic acid {3-[1-(toluene-4-sulfonyl)-pyrrolidin-2-yl]-propyl}-amide Acylation of (RS)-[1-(toluene-4-sulfonyl)-pyrrolidin-2-yl]-propylamine (see examples 33 and 87) according to the general method of example 6c yielded the title compound as a colorless oil, MS: m/e=351.3 (M+H$^+$).

EXAMPLE 88

(2RS,5RS)-2-{3-[5-(4-Fluoro-phenyl)-1-(toluene-4-sulfonyl)-pyrrolidin-2-yl]-propyl}-2H-tetrazole The title compound, colorless oil, MS: m/e=430.5 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 1H-tetrazole.

EXAMPLE 89

(2RS,5RS)-1-{3-[5-(4-Fluoro-phenyl)-1-(toluene-4-sulfonyl)-pyrrolidin-2-yl]-propyl}-1H-tetrazole The title compound, colorless oil, MS: m/e=430.5 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 1H-tetrazole.

EXAMPLE 90

(2RS,5RS)-N-{3-[5-(4-Fluoro-phenyl)-1-(toluene-4-sulfonyl)-pyrrolidin-2-yl]-propyl}-isobutyramide Acylation of (2RS,5RS)-[5-(4-fluoro-phenyl)-1-(toluene-4-sulfonyl)-pyrrolidin-2-yl]-propylamine according to the general method of example 6c yielded the title compound as a colorless oil, MS: m/e=447.4 (M+H$^+$).

EXAMPLE 91

(2RS,5RS)-1-{3-[5-(4-Fluoro-phenyl)-1-(toluene-4-sulfonyl)-pyrrolidin-2-yl]-propyl}-4-methyl-1H-imidazole The title compound, colorless oil, MS: m/e=442.2 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 4-methyl-1H-imidazole.

EXAMPLE 92

(2RS,5RS)-1-{3-[5-(4-Fluoro-phenyl)-1-(toluene-4-sulfonyl)-pyrrolidin-2-yl]-propyl}-2-methyl-1H-imidazole The title compound, colorless oil, MS: m/e=442.2 (M+H$^+$), was prepared in accordance with the general method of example 82b from (2RS,5RS)-2-(3-chloro-propyl)- 5-(4-fluoro-phenyl)-1-(toluene-4-sulfonyl)-pyrrolidine and 2-methyl-1H-imidazole.

EXAMPLE 93

(2RS,5RS)-2-{3-[5-(4-Fluoro-phenyl)-1-(toluene-4-sulfonyl)-pyrrolidin-2-yl]-propyl}-5-methyl-2H-tetrazole The title compound, colorless oil, MS: m/e=444.4 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 5-methyl-1H-tetrazole.

EXAMPLE 94

(2RS,5RS)-1-{3-[5-(4-Fluoro-phenyl)-1-(toluene-4-sulfonyl)-pyrrolidin-2-yl]-propyl}-5-methyl-1H-tetrazole The title compound, colorless oil, MS: m/e=444.4 (M+H$^+$), was prepared in accordance with the general method of example 82b from (2RS,5RS)-2-(3-chloro-propyl)-5-(4-fluoro-phenyl)-1-(toluene-4-sulfonyl)-pyrrolidine and 5-methyl-1H-tetrazole.

EXAMPLE 95

(2RS,5SR)-3-Cyclopropyl-5-[5-(4-fluoro-phenyl)-1-(toluene-4-sulfonyl)-pyrrolidin-2-ylmethyl]-[1,2,4]oxadiazole The title compound, white solid, m.p. 102° C. and MS: m/e=442.3 (M$^+$), was prepared in accordance with the general method of example 13 from N-hydroxy-cyclopropane-carboxamidine and (2RS,5SR)-3-[5-(4-fluoro-phenyl)-1-(toluene-4-sulfonyl)-pyrrolidin-2-yl]-acetic acid which was prepared by hydrolysis of (2RS,5SR)-[5-(4-fluoro-phenyl)-1-(toluene-4-sulfonyl)-pyrrolidin-2-yl]-acetonitrile.

EXAMPLE 96

(2RS,5SR)-5-[5-(4-Fluoro-phenyl)-1-(toluene-4-sulfonyl)-pyrrolidin-2-ylmethyl]-3-methyl-[1,2,4]oxadiazole The title compound, white solid, m.p. 103° C. and MS: m/e=416.2 (M+), was prepared in accordance with the general method of example 13 from N-hydroxy-acetamidine and (2RS,5SR)-3-[5-(4-fluoro-phenyl)-1-(toluene-4-sulfonyl)-pyrrolidin-2-yl]-acetic acid.

EXAMPLE 97

(2RS,5SR)-3-[5-(4-Fluoro-phenyl)-1-(toluene-4-sulfonyl)-pyrrolidin-2-ylmethyl]-1-methyl-1H-[1,2,4]triazole The title compound, light yellow oil, MS: m/e=415.1 (M+H+), was prepared in accordance with the general method of example 26 from (2RS,5RS)-4-[5-(4-fluoro-phenyl)-1-(toluene-4-sulfonyl)-pyrrolidin-2-yl]-acetonitrile and methylhydrazine.

EXAMPLE 98

(2RS,5SR)-2-[5-(4-Fluoro-phenyl)-1-(toluene-4-sulfonyl)-pyrrolidin-2-yl]-ethanol Reduction of (2RS,5SR)-3-[5-(4-fluoro-phenyl)-1-(toluene-4-sulfonyl)-pyrrolidin-2-yl]-acetic acid methyl ester, prepared by esterification of (2RS,5SR)-3-[5-(4-fluoro-phenyl)-1-(toluene-4-sulfonyl)-pyrrolidin-2-yl]-acetic acid, with lithium aluminum hydride (1.5 eq.) in THF at RT, aqueous work-up and crystallization from EE/hexane yielded the title compound, white solid, m.p. 129° C. and MS: m/e=364.1 (M+H+).

EXAMPLE 99

(2RS,5SR)-1-{2-[5-(4-Fluoro-phenyl)-1-(toluene-4-sulfonyl)-pyrrolidin-2-yl]-ethyl}-1H-imidazole The title compound, colorless oil, MS: m/e=414.1 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine, prepared from (2RS,5SR)-2-[5-(4-fluoro-phenyl)-1-(toluene-4-sulfonyl)-pyrrolidin-2-yl]-ethanol according to the general method of example 5, and 1H-imidazole.

EXAMPLE 100

(2RS,5SR)-1-{2-[5-(4-Fluoro-phenyl)-1-(toluene-4-sulfonyl)-pyrrolidin-2-yl]-ethyl}-1H-pyrazole The title compound, white solid, m.p.=121° C. and MS: m/e=414.2 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 1H-pyrazole.

EXAMPLE 101

(2RS,5SR)-2-{2-[5-(4-Fluoro-phenyl)-1-(toluene-4-sulfonyl)-pyrrolidin-2-yl]-ethyl}-2H-tetrazole The title compound, colorless oil, MS: m/e=416.2 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 1H-tetrazole.

EXAMPLE 102

(2RS,5SR)-1-{2-[5-(4-Fluoro-phenyl)-1-(toluene-4-sulfonyl)-pyrrolidin-2-yl]-ethyl}-1H-tetrazole The title compound, colorless oil, MS: m/e=416.1 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 1H-tetrazole.

EXAMPLE 103

(2RS,5SR)-1-{2-[5-(4-Fluoro-phenyl)-1-(toluene-4-sulfonyl)-pyrrolidin-2-yl]-ethyl}-1H-[1,2,4]triazole The title compound, colorless oil, MS: m/e=415.1 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 1H-triazole.

EXAMPLE 104

(2RS,5SR)-2-{2-[5-(4-Fluoro-phenyl)-1-(toluene-4-sulfonyl)-pyrrolidin-2-yl]-ethyl}-5-methyl-2H-tetrazole The title compound, colorless oil, MS: m/e=430.4 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 5-methyl-1H-tetrazole.

EXAMPLE 105

(2RS,5SR)-1-{2-[5-(4-Fluoro-phenyl)-1-(toluene-4-sulfonyl)-pyrrolidin-2-yl]-ethyl}-5-methyl-1H-tetrazole The title compound, colorless oil, MS: m/e=430.4 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 5-methyl-1H-tetrazole.

EXAMPLE 106

(2RS,5SR)-1-{2-[5-(4-Fluoro-phenyl)-1-(toluene-4-sulfonyl)-pyrrolidin-2-yl]-ethyl}-4-methyl-1H-imidazole The title compound, light yellow oil, MS: m/e=428.5 (M+H+), was prepared in accordance with the general method of example 82b from (2RS,5RS)-2-(2-chloro-ethyl)-5-(4-fluoro-phenyl)-1-(toluene-4-sulfonyl)-pyrrolidine and 4-methyl-1H-imidazole.

EXAMPLE 107

(2RS,5SR)-1-{2-[5-(4-Fluoro-phenyl)-1-(toluene-4-sulfonyl)-pyrrolidin-2-yl]-ethyl}-2-methyl-1H-imidazole The title compound, light yellow oil, MS: m/e=428.5 (M+H$^+$), was prepared in accordance with the general method of example 82b from (2RS,5RS)-2-(2-chloro-ethyl)-5-(4-fluoro-phenyl)-1-(toluene-4-sulfonyl)-pyrrolidine and 4-methyl-1H-imidazole.

EXAMPLE 108

(RS)-1-{3-[1-(Toluene-4-sulfonyl)-pyrrolidin-2-yl]-propyl}-1H-[1,2,4]triazole a) (RS)-3-[1-(toluene-4-sulfonyl)-pyrrolidin-2-yl]-propanol Reduction of (RS)-3-[1-(toluene-4-sulfonyl)-pyrrolidin-2-yl]-propionic acid methyl ester with lithium aluminum hydride (1.5 eq.) in THF at RT, aqueous work-up and crystallization from diethyl ether/hexane yielded (RS)-3-[1-(toluene-4-sulfonyl)-pyrrolidin-2-yl]-propanol, colorless oil, MS: m/e=284.2 (M+H$^+$).

b) (RS)-1-{3-[1-(Toluene-4-sulfonyl)-pyrrolidin-2-yl]-propyl}-1H-[1,2,4]triazole The title compound, colorless oil, MS: m/e=335.3 (M+H$^+$), was prepared in accordance with the general method of example 82b from (RS)-2-(3-chloro-propyl)-1-(toluene-4-sulfonyl)-pyrrolidine, prepared from (RS)-3-[1-(toluene-4-sulfonyl)-pyrrolidin-2-yl]-propanol according to the general method of example 5, and 1H-triazole.

EXAMPLE 109

(2RS,5SR)-2-{2-[5-(4-Fluoro-phenyl)-1-(toluene-4-sulfonyl)-pyrrolidin-2-yl]-ethyl}-1H-imidazole a) (2RS,5SR)-2-{2-[5-(4-fluoro-phenyl)-1-(toluene-4-sulfonyl)-pyrrolidin-2-yl]-ethyl}-carboxaldehyde Oxidation of (2RS,5RS)-3-[5-(4-fluoro-phenyl)-1-(toluene-4-sulfonyl)-pyrrolidin-2-yl]-propan-1-ol according to the general method of example 29a and purification of the crude product by column cromatography on silica gel (ethyl acetate/hexane 1:1) gave (2RS,5SR)-2-{2-[5-(4-fluoro-phenyl)-1-(toluene-4-sulfonyl)-pyrrolidin-2-yl]-ethyl}-carboxaldehyde as a light yellow oil.

b) (2RS,5SR)-2-{2-[5-(4-Fluoro-phenyl)-1-(toluene-4-sulfonyl)-pyrrolidin-2-yl]-ethyl}-1H-imidazole To a cooled (0° C.) and stirred solution of (2RS,5SR)-2-{2-[5-(4-fluoro-phenyl)-1-(toluene-4-sulfonyl)-pyrrolidin-2-yl]-ethyl}-carboxaldehyde (1.30 g, 3.46 mmol) was added glyoxal (0.8 ml, 40% in water) and subsequently ammonium hydroxide (1.15 ml, 25% in water). The reaction mixture was stirred 30 min at 0° C. and 15 h by RT, poured into water (30 ml) and extracted with dichloromethane (2×50 ml). The combined organic layers were washed with brine (30 ml), dried (MgSO$_4$) and evaporated. The crude product was purified by column chromatography on silica gel (dichloromethane/methanol 19:1) to give the title compound (1.18 g, 82%) as a white foam, MS: m/e=414.3 (M+H$^+$).

EXAMPLE 110

(2RS,5RS)-2-{3-[5-(4-Fluoro-phenyl)-1-(toluene-4-sulfonyl)-pyrrolidin-2-yl]-propyl}-1H-imidazole The title compound, white foam, MS: m/e=428.5 (M+H$^+$), was prepared in accordance to the general method of example 109 from (2RS,5RS)-3-[5-(4-fluoro-phenyl)-1-(toluene-4-sulfonyl)-pyrrolidin-2-yl]-butan-1-ol.

EXAMPLE 111

(2RS,5SR)-2-{2-[5-(4-Fluoro-phenyl)-1-(toluene-4-sulfonyl)-pyrrolidin-2-yl]-ethyl}-1-methyl-1H-imidazole The title compound, light yellow oil, MS: m/e=428.5 (M+H$^+$), was prepared by methylation of (2RS,5SR)-2-{2-[5-(4-fluoro-phenyl)-1-(toluene-4-sulfonyl)-pyrrolidin-2-yl]-ethyl}-1H-imidazole in accordance with the general method of example 8 (methyl iodide, sodium hydride).

EXAMPLE 112

(2RS,5RS)-2-{3-[5-(4-Fluoro-phenyl)-1-(toluene-4-sulfonyl)-pyrrolidin-2-yl]-propyl}-1-methyl-1H-imidazole The title compound, light yellow oil, MS: m/e=442.2 (M+H$^+$), was prepared by methylation of (2RS,5SR)-2-{2-[5-(4-fluoro-phenyl)-1-(toluene-4-sulfonyl)-pyrrolidin-2-yl]-propyl}-1H-imidazole in accordance with the general method of example 8 (methyl iodide, sodium hydride).

EXAMPLE 113

(2R,5S)-2-{2-[5-(4-Fluoro-phenyl)-1-(toluene-4-sulfonyl)-pyrrolidin-2-yl]-ethyl}-1H-imidazole The title compound, white foam, MS: m/e=414.1 (M+H$^+$) and $[\alpha]_D^{20}$=96.93° (c=1.0399 in chloroform) was prepared from (2R,5S)-3-[5-(4-fluoro-phenyl)-1-(toluene-4-sulfonyl)-pyrrolidin-2-yl]-propan-1-ol in accordance with the general method of example 109.

EXAMPLE 114

(2R,5S)-2-{2-[5-(4-Fluoro-phenyl)-1-(toluene-4-sulfonyl)-pyrrolidin-2-yl]-ethyl}-1-methyl-1H-imidazole The title compound, light yellow oil, MS: m/e=428.2 (M+H$^+$) and $[\alpha]_D^{20}$=−69.7° (c=0.2770 in chloroform), was prepared by methylation of (2R,5S)-2-{2-[5-(4-fluoro-phenyl)-1-(toluene-4-sulfonyl)-pyrrolidin-2-yl]-ethyl}-1H-imidazole in accordance with the general method of example 8 (methyl iodide, sodium hydride).

EXAMPLE 115

(2R,5S)-1-{3-[5-(4-Fluoro-phenyl)-1-(toluene-4-sulfonyl)-pyrrolidin-2-yl]-propyl}-1H-[1,2,4]triazole The title compound, colorless oil, MS: m/e=429.2 (M+H$^+$) and $[D]_D^{20}$=−73.1° (c=0.3011 in chloroform), was prepared in accordance with the general method of example 82b from (2R,5S)-2-(3-chloro-propyl)-5-(4-fluoro-phenyl)-

1-(toluene-4-sulfonyl)-pyrrolidine, which was prepared from (2R,5S)-3-[5-(4-fluoro-phenyl)-1-(toluene-4-sulfonyl)-pyrrolidin-2-yl]-propanol according to the general method of example 5, and 1H-triazole.

EXAMPLE 116

(2S,5S)-1-{3-[5-(4-Fluoro-phenyl)-1-(toluene-4-sulfonyl)-pyrrolidin-2-yl]-propyl}-1H-imidazole The title compound, colorless oil, MS: m/e=428.5 (M+H$^+$) and [α]$_D^{20}$=−68.5° (c=0.3050 in chloroform), was prepared in accordance with the general method of example 82b from (2R,5S)-2-(3-chloro-propyl)-5-(4-fluoro-phenyl)-1-(toluene-4-sulfonyl)-pyrrolidine and 1H-imidazole.

EXAMPLE 117

(2S,5S)-1-{3-[5-(4-Fluoro-phenyl)-1-(toluene-4-sulfonyl)-pyrrolidin-2-yl]-propyl}-1H-pyrazole The title compound, colorless oil, MS: m/e=428.5 (M+H$^+$) and [α]$_D$=−67.7° (c=0.2955 in chloroform), was prepared in accordance with the general method of example 82b from (2R,5S)-2-(3-chloro-propyl)-5-(4-fluoro-phenyl)-1-(toluene-4-sulfonyl)-pyrrolidine and 1H-pyrazole.

EXAMPLE 118

(2R,5S)-2-(4-Fluoro-phenyl)-5-(3-methoxy-propyl)-1-(toluene-4-sulfonyl)-pyrrolidine The title compound, colorless oil, MS: m/e=392.1 (M+H$^+$) and [α]$_D^{20}$=−82.7° (c=0.2682 in chloroform), was prepared in accordance with the general method of example 8 from (2S,5S)-3-[5-(4-fluoro-phenyl)-1-(toluene-4-sulfonyl)-pyrrolidin-2-yl]-propan-1-ol.

EXAMPLE 119

(2RS,5SR)-2-(2-Ethoxy-ethyl)-5-(4-fluoro-phenyl)-1-(toluene-4-sulfonyl)-pyrrolidine The title compound, light yellow oil, MS: m/e=392.2 (M+H$^+$), was prepared in accordance with the general method of example 8 from (2RS,5SR)-3-[5-(4-fluoro-phenyl)-1-(toluene-4-sulfonyl)-pyrrolidin-2-yl]-ethan-1-ol and ethyliodide.

EXAMPLE 120

(2RS,5SR)-2-(2-Cyclopropylmethoxy-ethyl)-5-(4-fluoro-phenyl)-1-(toluene-4-sulfonyl)-pyrrolidine The title compound, light yellow oil, MS: m/e=418.3 (M+H$^+$), was prepared in accordance with the general method of example 8 from (2RS,5SR)-3-[5-(4-fluoro-phenyl)-1-(toluene-4-sulfonyl)-pyrrolidin-2-yl]-ethan-1-ol and cyclopropylmethylbromide.

EXAMPLE 121

(2S,5S)-5-{3-[5-(4-Fluoro-phenyl)-1-(toluene-4-sulfonyl)-pyrrolidin-2-yl]-propyl}-1-methyl-1H-[1,2,4]triazole The title compound, colorless oil, MS: m/e=443.2 (M+H$^+$) and [α]$_D^{20}$=−68.8° (c=0.3443 in chloroform), was prepared in accordance with the general method of example 26 from (2S,5S)-4-[5-(4-fluoro-phenyl)-1-(toluene-4-sulfonyl)-pyrrolidin-2-yl]-butyronitrile and methylhydrazine.

EXAMPLE 122

(2S,5R)-3-{3-[5-(4-Fluoro-phenyl)-1-(toluene-4-sulfonyl)-pyrrolidin-2-yl]-propyl}-1-methyl-1H-[1,2,4]triazole The title compound, colorless oil, MS: m/e=443.2 (M+H$^+$) and [α]$_D^{20}$=−53.7° (c=0.3929 in chloroform), was prepared in accordance with the general method of example 26 from (2S,5S)-4-[5-(4-fluoro-phenyl)-1-(toluene-4-sulfonyl)-pyrrolidin-2-yl]-butyronitrile and methylhydrazine.

EXAMPLE 123

(2RS,5RS)-2-{3-[5-(4-Fluoro-phenyl)-1-(toluene-4-sulfonyl)-pyrrolidin-2-yl]-propyl}-4,6-dimethyl-pyrimidine a) (2RS,5RS)-4-[5-(4-fluoro-phenyl)-1-(toluene-4-sulfonyl)-pyrrolidin-2-yl]-N-butyramidine (2RS,5RS)-4-[5-(4-Fluoro-phenyl)-1-(toluene-4-sulfonyl)-pyrrolidin-2-yl]-N-hydroxy-butyramidine (1.1 g, 2.62 mmol) was dissolved in EtOH (50 ml) and acetic acid (5 ml) and hydrogenated on Ra—Ni at room temperature for 2 h. The catalyst was filtered off, the filtrate evaporated and the crude product crystallized from saturated NaHCO$_3$ solution to give (2RS,5RS)-4-[5-(4-fluoro-phenyl)-1-(toluene-4-sulfonyl)-pyrrolidin-2-yl]-N-butyramidine (0.81 g, 76%) as a light brown solid.

b) (2RS,5RS)-2-{3-[5-(4-fluoro-phenyl)-1-(toluene-4-sulfonyl)-pyrrolidin-2-yl]-propyl}-4,6-dimethyl-pyrimidine A stirred solution of (2RS,5RS)-4-[5-(4-fluoro-phenyl)-1-(toluene-4-sulfonyl)-pyrrolidin-2-yl]-N-butyramidine (0.35 g, 0.87 mmol) in pentan-2,4-dione (7 ml) was heated for 3 h at 125° C. Evaporation and purification by column chromatography on silica gel (ethyl acetate) yielded the title compound (0.15 g, 38%) as a light yellow oil, MS: m/e=468.3 (M+H$^+$).

EXAMPLE 124

(2RS,5SR)-2-{2-[5-(4-Fluoro-phenyl)-1-(toluene-4-sulfonyl)-pyrrolidin-2-yl]-ethyl}-4,6-dimethyl-pyrimidine The title compound, light yellow oil, MS: m/e=454.3 (M+H$^+$), was prepared in accordance with the general method of example 123b) from (2RS,5RS)-4-[5-(4-fluoro-phenyl)-1-(toluene-4-sulfonyl)-pyrrolidin-2-yl]-N-propionamidine.

EXAMPLE 125

(2RS,5RS)-2-{3-[5-(4-Fluoro-phenyl)-1-(toluene-4-sulfonyl)-pyrrolidin-2-yl]-propyl}-pyrimidine A stirred solution of (2RS,5RS)-4-[5-(4-fluoro-phenyl)-1-(toluene-4-sulfonyl)-pyrrolidin-2-yl]-N-butyramidine (0.33 g, 0.82 mmol) in 1,1,3,3-tetraethoxy-propane (7 ml) and DMF (1.5 ml) was heated for 1 h at 150° C. Evaporation and purification by column chromatography on silica gel (dichloromethane/MeOH 98:2) yielded the title compound (73 mg, 20%) as a light brown oil, MS: m/e=440.2 (M+H$^+$).

EXAMPLE 126

(2RS,5SR)-2-{2-[5-(4-Fluoro-phenyl)-1-(toluene-4-sulfonyl)-pyrrolidin-2-yl]-ethyl}-pyrimidine The title compound, light orange oil, MS: m/e=426.3 (M+H$^+$), was prepared in accordance with the general method of example 125 from (2RS,5RS)-4-[5-(4-fluoro-phenyl)-1-(toluene-4-sulfonyl)-pyrrolidin-2-yl]-N-propionamidine.

EXAMPLE 127

(2RS,5SR)-2-{2-[5-(4-Fluoro-phenyl)-1-(toluene-4-sulfonyl)-pyrrolidin-2-yl]-ethyl}-[1,3,4]oxadiazole a) (2RS,5SR)-3-[5-(4-fluoro-phenyl)-1-(toluene-4-sulfonyl)-pyrrolidin-2-yl]-propionic acid hydrazide To a stirred solution of (2RS,5SR)-3-[5-(4-fluoro-phenyl)-1-(toluene-4-sulfonyl)-pyrrolidin-2-yl]-propionic acid methyl ester (1.5 g, 3.7 mmol) in MeOH (15 ml) was added hydrazine hydrate (0.54 ml, 11.1 mmol) and p-TsOH (10 mg) and the reaction mixture was heated under reflux conditions for 24 h. Evaporation and purification by column chromatography on silica gel (dichloromethane/MeOH 19:1) yielded (2RS,5SR)-3-[5-(4-fluoro-phenyl)-1-(toluene-4-sulfonyl)-pyrrolidin-2-yl]-propionic acid hydrazide (1.25 g, 83%) as a white solid.

b) (2RS,5SR)-2-{2-[5-(4-Fluoro-phenyl)-1-(toluene-4-sulfonyl)-pyrrolidin-2-yl]-ethyl}-[1,3,4]oxadiazole A stirred solution of (2RS,5SR)-3-[5-(4-fluoro-phenyl)-1-(toluene-4-sulfonyl)-pyrrolidin-2-yl]-propionic acid hydrazide (0.4 g, 0.99 mmol) in triethyl orthoformiate (10 ml) was heated under reflux conditions for 13 h, evaporated and purified by column chromato-graphy on silica gel (dichloromethane/MeOH 98:2). Further purification by crystallization from ethyl acetate/hexane gave the title compound (276 mg, 67%) as an off-white solid, m.p.=138° C. and MS: m/e=416.3 (M+H$^+$).

EXAMPLE 128

(2RS,5SR)-2-{2-[5-(4-Fluoro-phenyl)-1-(toluene-4-sulfonyl)-pyrrolidin-2-yl]-ethyl}-5-methyl-[1,3,4]oxadiazole The title compound, light yellow oil, MS: m/e=430.2 (M+H$^+$), was prepared in accordance with the general method of example 127 from (2RS,5SR)-3-[5-(4-fluoro-phenyl)-1-(toluene-4-sulfonyl)-pyrrolidin-2-yl]-propionic acid hydrazide and triethyl orthoacetate.

EXAMPLE 129

(2RS,5SR)-5-{2-[5-(4-Fluoro-phenyl)-1-(toluene-4-sulfonyl)-pyrrolidin-2-yl]-ethyl}-oxazole A stirred mixture of (2RS,5S)-3-[5-(4-fluoro-phenyl)-1-(toluene-4-sulfonyl)-pyrrolidin-2-yl]-propionaldehyde (375 mg, 1.0 mmol, prepared from the corresponding alcohol by oxidation in accordance with the general method of example 29a), tosylmethyl-isocyanate (199 mg, 1.0 mmol), potassium carbonate (207 mg, 1.5 mmol) and MeOH (10 ml) was heated under reflux conditions for 35 h, evaporated and purified by column chromato-graphy on silica gel (ethyl acetate/hexane 4:1) to give the title compound (100 mg, 24%) as a light yellow oil, MS: m/e=415.3 (M+H$^+$).

EXAMPLE 130

(2RS,5RS)-2-(4-Fluoro-phenyl)-5-(4-methoxy-butyl)-1-(toluene-4-sulfonyl)-pyrrolidine The title compound, light yellow oil, MS: m/e=406.3 (M+H$^+$), was prepared in accordance with the general method of example 8 from (2RS,5RS)-3-[5-(4-fluoro-phenyl)-1-(toluene-4-sulfonyl)-pyrrolidin-2-yl]-butan-1-ol and methyliodide.

EXAMPLE 131

(2RS,5RS)-2-(4-Ethoxy-butyl)-5-(4-fluoro-phenyl)-1-(toluene-4-sulfonyl)-pyrrolidine The title compound, colorless oil, MS: m/e=420.4 (M+H$^+$), was prepared in accordance with the general method of example 8 from (2RS,5RS)-3-[5-(4-fluoro-phenyl)-1-(toluene-4-sulfonyl)-pyrrolidin-2-yl]-butan-1-ol and ethyliodide.

EXAMPLE 132

(2RS,5RS)-2-{3-[5-(4-Fluoro-phenyl)-1-(toluene-4-sulfonyl)-pyrrolidin-2-yl]-propyl}-[1,3,4]oxadiazole The title compound, light yellow oil, MS: m/e=430.1 (M+H$^+$), was prepared in accordance with the general method of example 127 from (2RS,5RS)-3-[5-(4-fluoro-phenyl)-1-(toluene-4-sulfonyl)-pyrrolidin-2-yl]-butyric acid hydrazide and triethyl orthoformiate.

EXAMPLE 133

(2RS,5RS)-2-{3-[5-(4-Fluoro-phenyl)-1-(toluene-4-sulfonyl)-pyrrolidin-2-yl]-propyl}-5-methyl-[1,3,4]oxadiazole The title compound, light yellow oil, MS: m/e=444.2 (M+H$^+$), was prepared in accordance with the general method of example 127 from (2RS,5SR)-3-[5-(4-fluoro-phenyl)- 1-(toluene-4-sulfonyl)-pyrrolidin-2-yl]-butyric acid hydrazide and triethyl orthoacetate.

EXAMPLE 134

(2RS,5RS)-1-{4-[5-(4-Fluoro-phenyl)-1-(toluene-4-sulfonyl)-pyrrolidin-2-yl]-butyl}-1H-[1,2,4]triazole The title compound, colorless oil, MS: m/e=443.3 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 1H-triazole.

EXAMPLE 135

(2RS,5SR)-5-[5-(4-Fluoro-phenyl)-1-(toluene-4-sulfonyl)-pyrrolidin-2-ylmethyl]-oxazole The title compound, light yellow oil, MS: m/e=401.4 (M+H$^+$), was prepared in accordance with the general

EXAMPLE 136

(2RS,5RS)-1-{4-[5-(4-Fluoro-phenyl)-1-(toluene-4-sulfonyl)-pyrrolidin-2-yl]-butyl}-1H-pyrazole The title compound, colorless oil, MS: m/e=442.4 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 1H-pyrazole.

EXAMPLE 137

(2RS,5SR)-2-[5-(4-Fluoro-phenyl)-1-(toluene-4-sulfonyl)-pyrrolidin-2-yl]-[1,3,4]oxadiazole The title compound, light yellow oil, MS: m/e=388.2 (M+H$^+$), was prepared in accordance with the general method of example 127 from (2RS,5SR)-5-(4-Fluoro-phenyl)-1-(toluene-4-sulfonyl)-pyrrolidine-2-carboxylic acid hydrazide and triethyl orthoformiate.

EXAMPLE 138

(2RS,5SR)-2-[5-(4-Fluoro-phenyl)-1-(toluene-4-sulfonyl)-pyrrolidin-2-ylmethyl]-[1,3,4]oxadiazole The title compound, light yellow oil, MS: m/e=402.4 (M+H$^+$), was prepared in accordance with the general method of example 127 from (2RS,5SR)-3-[5-(4-fluoro-phenyl)-1-(toluene-4-sulfonyl)-pyrrolidin-2-yl]-acetic acid hydrazide and triethyl orthoformiate.

EXAMPLE 139

(2RS,5RS)-1-{4-[5-(4-Fluoro-phenyl)-1-(toluene-4-sulfonyl)-pyrrolidin-2-yl]-butyl}-1H-imidazole The title compound, colorless oil, MS: m/e=442.4 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 1H-imidazole.

EXAMPLE 140

(2RS,5RS)-1-{4-[5-(4-Fluoro-phenyl)-1-(toluene-4-sulfonyl)-pyrrolidin-2-yl]-butyl}-4-methyl-1H-imidazole The title compound, colorless oil, MS: m/e=456.5 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 4-methyl-1H-imidazole.

EXAMPLE 141

(2RS,5SR)-2-[5-(4-Fluoro-phenyl)-1-(toluene-4-sulfonyl)-pyrrolidin-2-yl-methyl]-5-methyl-[1,3,4]oxadiazole The title compound, light yellow oil, MS: m/e=416.3 (M+H$^+$), was prepared in accordance with the general method of example 127 from (2RS,5SR)-3-[5-(4-fluoro-phenyl)-1-(toluene-4-sulfonyl)-pyrrolidin-2-yl]-acetic acid hydrazide and triethyl orthoacetate.

EXAMPLE 142

(2RS,5RS)-4-[5-(4-Fluoro-phenyl)-1-(toluene-4-sulfonyl)-pyrrolidin-2-yl]-butan-1-ol Reduction of (2RS,5RS)-4-[5-(4-fluoro-phenyl)-1-(toluene-4-sulfonyl)-pyrrolidin-2-yl]-butyric acid methyl ester with lithium aluminum hydride (1.5 eq.) in THF at RT, aqueous work-up and purification by column chromatography yielded the title compound as a colorless oil, MS: m/e=392.2 (M+H$^+$).

EXAMPLE 143

(2RS,5RS)-2-{4-[5-(4-Fluoro-phenyl)-1-(toluene-4-sulfonyl)-pyrrolidin-2-yl]-butyl}-2H-tetrazole The title compound, colorless oil, MS: m/e=444.3 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 1H-tetrazole.

EXAMPLE 144

(2RS,5RS)-1-{4-[5-(4-Fluoro-phenyl)-1-(toluene-4-sulfonyl)-pyrrolidin-2-yl]-butyl}-1H-tetrazole The title compound, colorless oil, MS: m/e=444.4 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 1H-tetrazole.

EXAMPLE 145

(2RS,5RS)-2-{4-[5-(4-Fluoro-phenyl)-1-(toluene-4-sulfonyl)-pyrrolidin-2-yl]-butyl}-5-methyl-2H-tetrazole The title compound, pale yellow oil, MS: m/e=458.4 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 5-methyl-1H-tetrazole.

EXAMPLE 146

(2RS,5RS)-1-{4-[5-(4-Fluoro-phenyl)-1-(toluene-4-sulfonyl)-pyrrolidin-2-yl]-butyl}-5-methyl-1H-tetrazole The title compound, colorless oil, MS: m/e=458.4 (M+H$^+$), was prepared in accordance with the general method of example 82b from (2RS,5RS)-2-(4-chloro-butyl)-5-(4-fluoro-phenyl)-1-(toluene-4-sulfonyl)-pyrrolidine and 5-methyl-1H-tetrazole.

EXAMPLE 147

(2RS,5RS)-5-[5-(4-Fluoro-phenyl)-1-(toluene-4-sulfonyl)-pyrrolidin-2-yl]-pentan-1-ol Reduction of (2RS,5RS)-5-[5-(4-fluoro-phenyl)-1-(toluene-4-sulfonyl)-pyrrolidin-2-yl]-pentanoic acid methyl ester with lithium aluminum hydride (1.5 eq.) in THF at RT, aqueous work-up and purification by column chromatography yielded the title compound as a light orange oil, MS: m/e=406.2 (M+H⁺).

EXAMPLE 148

(2RS,5RS)-1-{5-[5-(4-Fluoro-phenyl)-1-(toluene-4-sulfonyl)-pyrrolidin-2-yl]-pentyl}-1H-imidazole The title compound, colorless oil, MS: m/e=456.5 (M+H⁺), was prepared in accordance with the general method of example 82b from (2RS,5RS)-2-(4-chloro-pentyl)-5-(4-fluoro-phenyl)-1-(toluene-4-sulfonyl)-pyrrolidine and 1H-imidazole.

EXAMPLE 149

(2RS,5RS)-1-{5-[5-(4-Fluoro-phenyl)-1-(toluene-4-sulfonyl)-pyrrolidin-2-yl]-pentyl}-1H-[1,2,4]triazole The title compound, colorless oil, MS: m/e=457.1 (M+H⁺), was prepared in accordance with the general method of example 82b from (2RS,5RS)-2-(4-chloro-pentyl)-5-(4-fluoro-phenyl)-1-(toluene-4-sulfonyl)-pyrrolidine and 1H-triazole.

EXAMPLE 150

(2S,5S)-4-[5-(4-Fluoro-phenyl)-1-(toluene-4-sulfonyl)-pyrrolidin-2-yl]-butan-1-ol Reduction of (2S,5S)-4-[5-(4-fluoro-phenyl)-1-(toluene-4-sulfonyl)-pyrrolidin-2-yl]-butyric acid methyl ester with lithium aluminum hydride (1.5 eq.) in THF at RT, aqueous work-up and purification by column chromatography yielded the title compound as a colorless oil, MS: m/e=392.3 (M+H⁺) and $[\alpha]_D^{20}$=−80.1° (c=1.0870 in chloroform).

EXAMPLE 151

(2S,5S)-2-(4-Fluoro-phenyl)-5-(4-methoxy-butyl)-1-(toluene-4-sulfonyl)-pyrrolidine The title compound, colorless oil, MS: m/e=406.1 (M+H⁺) and $[\alpha]_D^{20}$=−76.2° (c=0.2558 in chloroform), was prepared in accordance with the general method of example 8 from (2S,5S)-3-[5-(4-fluoro-phenyl)-1-(toluene-4-sulfonyl)-pyrrolidin-2-yl]-butan-1-ol and methyliodide.

EXAMPLE 152

(2S,5S)-1-{4-[5-(4-Fluoro-phenyl)-1-(toluene-4-sulfonyl)-pyrrolidin-2-yl]-butyl}-1H-imidazole The title compound, colorless oil, MS: m/e=442.3 (M+H⁺) and $[\alpha]_D^{20}$=−64.3° (c=0.2673 in chloroform), was prepared in accordance with the general method of example 82b from (2S,5S)-2-(4-chloro-butyl)-5-(4-fluoro-phenyl)-1-(toluene-4-sulfonyl)-pyrrolidine and 1H-imidazole.

EXAMPLE 153

(2S,5S)-1-{4-[5-(4-Fluoro-phenyl)-1-(toluene-4-sulfonyl)-pyrrolidin-2-yl]-butyl}-1H-[1,2,4]triazole The title compound, colorless oil, MS: m/e=443.3 (M+H⁺) and $[\alpha]_D^{20}$=−72.5° (c=0.2358 in chloroform), was prepared in accordance with the general method of example 82b from (2S,5S)-2-(4-chloro-butyl)-5-(4-fluoro-phenyl)-1-(toluene-4-sulfonyl)-pyrrolidine and 1H-tetrazole.

EXAMPLE 154

(2R,5S)-2-{2-[5-(4-Fluoro-phenyl)-1-(toluene-4-sulfonyl)-pyrrolidin-2-yl]-ethyl}-[1,3,4]oxadiazole The title compound, light yellow oil, MS: m/e=416.1 (M+H⁺) and $[\alpha]_D^{20}$=−80.1° (c=0.2211 in chloroform), was prepared in accordance with the general method of example 127 from (2R,5S)-3-[5-(4-fluoro-phenyl)-1-(toluene-4-sulfonyl)-pyrrolidin-2-yl]-propionic acid hydrazide and triethyl orthoformiate.

EXAMPLE A

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

| | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

| | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of the formula

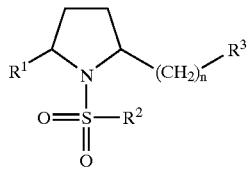

wherein
- $R^1$ is aryl, which is unsubstituted or substituted by halogen;
- $R^2$ is aryl, which is unsubstituted or substituted by halogen or lower alkyl;
- $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
- $R^4$ is cycloalkyl, phenyl or lower alkyl, which is unsubstituted or substituted by halogen
- R is lower alkyl;
- R' and R'" are lower alkyl or cycloalkyl-lower alkyl;
- R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
- n is an integer from 2 to 5;

or a pharmaceutically acceptable salt thereof.

2. A compound according to claim 1 wherein $R^2$ is phenyl unsubstituted or substituted by halogen or lower alkyl.

3. A compound according to claim 2 wherein $R^2$ is p-tolyl and n is 3.

4. A compound according to claim 1 wherein $R^3$ is N(R')—C(O)—$R^4$, or a 5-membered heteroaryl ring containing from 1 to 4 N or O heteroatoms, said ring being unsubstituted or substituted by lower alkyl or cycloalkyl.

5. The compound of claim 4, which is (RS)-N-{3-[1-(Toluene-4-sulfonyl)-pyrrolidin-2-yl]-propyl}-acetamide.

6. The compound of claim 4, which is (RS)-Cyclopropanecarboxylic acid {3-[1-(toluene-4-sulfonyl)-pyrrolidin-2-yl]-propyl}-amide.

7. The compound of claim 4, which is (RS)-1-{3-[1-(Toluene-4-sulfonyl)-pyrrolidin-2-yl]-propyl}-1H-[1,2,4]triazole.

8. A compound according to claim 1 wherein $R^1$ is phenyl or halo substituted phenyl and $R^2$ is phenyl, or halo substituted phenyl or lower alkyl substituted phenyl.

9. A compound according to claim 1 having the structure

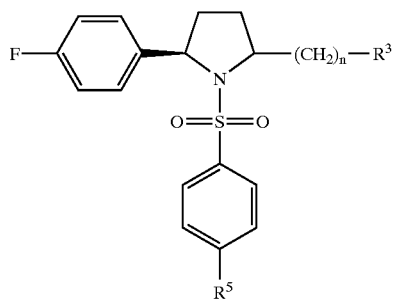

wherein wherein $R^5$ is hydrogen, halogen or lower alkyl.

10. A compound according to claim 9 wherein $R^3$ is N-hydroxy-amidino, —C(O)NR'R" or —N(R')—C(O)—$R^4$; $R^5$ is halogen and n is 2 or 3.

11. The compound of claim 10, which is (2RS,5SR)-N-{2-[1-(4-Chloro-benzenesulfonyl)-5-(4-fluoro-phenyl)-pyrrolidin-2-yl]-ethyl}-acetamide.

12. The compound of claim 10, which is (2RS,5SR)-Cyclopropanecarboxylic acid {2-[1-(4-chloro-benzenesulfonyl)-5-(4-fluoro-phenyl)-pyrrolidin-2-yl]-ethyl}-amide.

13. The compound of claim 10, which is (2RS,5SR)-3-[1-(4-Chloro-benzenesulfonyl)-5-(4-fluoro-phenyl)-pyrrolidin-2-yl]-propionamide.

14. The compound of claim 10, which is (2RS,5RS)-N-{3-[1-(4-Chloro-benzenesulfonyl)-5-(4-fluoro-phenyl)-pyrrolidin-2-yl]-propyl}-acetamide.

15. The compound of claim 10, which is (2RS,5SR)-3-[1-(4-Chloro-benzenesulfonyl)-5-(4-fluoro-phenyl)-pyrrolidin-2-yl]-propan-1-ol.

16. The compound of claim 10, which is (2RS,5SR)-5-{2-[1-(4-Chloro-benzenesulfonyl)-5-(4-fluoro-phenyl)-pyrrolidin-2-yl]-ethyl}-2-methyl-2H-tetrazole.

17. A compound according to claim 9 having the structure

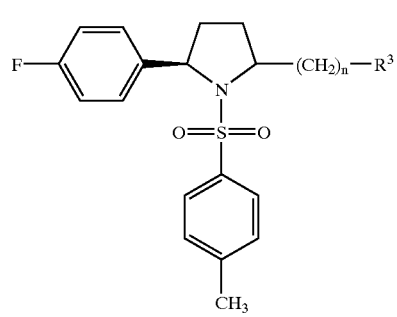

18. A compound according to claim 17 wherein $R^3$ is an unsubstituted 5-membered heteroaryl ring containing 1 to 4 from N or O heteroatoms.

19. A compound according to claim 18 wherein said unsubstituted 5-membered heteroaryl ring contains from 1 to 4 nitrogen atoms and n is 2.

20. The compound of claim 19, which is (2RS,5SR)-1-{2-[5-(4-Fluoro-phenyl)-1-(toluene-4-sulfonyl)-pyrrolidin-2-yl]-ethyl}-1H-imidazole.

21. The compound of claim 19, which is (2RS,5SR)-1-{2-[5-(4-Fluoro-phenyl)-1-(toluene-4-sulfonyl)-pyrrolidin-2-yl]-ethyl}-1H-pyrazole.

22. The compound of claim 19, which is (2RS,5SR)-2-{2-[5-(4-Fluoro-phenyl)-1-(toluene-4-sulfonyl)-pyrrolidin-2-yl]-ethyl}-2H-tetrazole.

23. The compound of claim 19, which is (2RS,5SR)-1-{2-[5-(4-Fluoro-phenyl)-1-(toluene-4-sulfonyl)-pyrrolidin-2-yl]-ethyl}-1H-tetrazole.

24. The compound of claim 19, which is (2RS,5SR)-1-{2-[5-(4-Fluoro-phenyl)-1-(toluene-4-sulfonyl)-pyrrolidin-2-yl]-ethyl}-1H-[1,2,4]triazole.

25. A compound according to claim 18 wherein said heteroaryl ring includes at least one oxygen atom and n is 2.

26. The compound of claim 25, which is (2RS,5SR)-2-{2-[5-(4-Fluoro-phenyl)-1-(toluene-4-sulfonyl)-pyrrolidin-2-yl]-ethyl}-5-methyl-[1,3,4]oxadiazole.

27. The compound of claim 25, which is (2RS,5SR)-5-{2-[5-(4-Fluoro-phenyl)-1-(toluene-4-sulfonyl)-pyrrolidin-2-yl]-ethyl}-oxazole.

28. A compound according to claim 18 wherein said unsubstituted 5-membered heteroaryl ring contains from 1 to 4 nitrogen atoms and n is 3, 4 or 5.

29. The compound of claim 28, which is (2RS,5RS)-1-{3-[5-(4-Fluoro-phenyl)-1-(toluene-4-sulfonyl)-pyrrolidin-2-yl]-propyl}-1H-[1,2,4]triazole.

30. The compound of claim 28, which is (2RS,5RS)-1-{3-[5-(4-Fluoro-phenyl)-1-(toluene-4-sulfonyl)-pyrrolidin-2-yl]-propyl}-1H-imidazole.

31. The compound of claim 28, which is (2RS,5RS)-1-{3-[5-(4-Fluoro-phenyl)-1-(toluene-4-sulfonyl)-pyrrolidin-2-yl]-propyl}-1H-pyrazole.

32. The compound of claim 28, which is (2RS,5RS)-2-{3-[5-(4-Fluoro-phenyl)-1-(toluene-4-sulfonyl)-pyrrolidin-2-yl]-propyl}-2H-tetrazole.

33. The compound of claim 28, which is (2RS,5RS)-1-{3-[5-(4-Fluoro-phenyl)-1-(toluene-4-sulfonyl)-pyrrolidin-2-yl]-propyl}-1H-tetrazole.

34. The compound of claim 28, which is (2RS,5RS)-1-{4-[5-(4-Fluoro-phenyl)-1-(toluene-4-sulfonyl)-pyrrolidin-2-yl]-butyl}-1H-pyrazole.

35. The compound of claim 28, which is (2RS,5RS)-2-{4-[5-(4-Fluoro-phenyl)-1-(toluene-4-sulfonyl)-pyrrolidin-2-yl]-butyl}-2H-tetrazole.

36. The compound of claim 28, which is (2RS,5RS)-1-{4-[5-(4-Fluoro-phenyl)-1-(toluene-4-sulfonyl)-pyrrolidin-2-yl]-butyl}-1H-tetrazole.

37. The compound of claim 28, which is (2RS,5RS)-1-{5-[5-(4-Fluoro-phenyl)-1-(toluene-4-sulfonyl)-pyrrolidin-2-yl]-pentyl}-1H-imidazole.

38. The compound of claim 28, which is (2RS,5RS)-1-{5-[5-(4-Fluoro-phenyl)-1-(toluene-4-sulfonyl)-pyrrolidin-2-yl]-pentyl}-1H-[1,2,4]triazole.

39. The compound of claim 28, which is (2RS,5RS)-1-{4-[5-(4-Fluoro-phenyl)-1-(toluene-4-sulfonyl)-pyrrolidin-2-yl]-butyl}-1H-imidazole.

40. The compound of claim 28, which is (2RS,5RS)-1-{4-[5-(4-Fluoro-phenyl)-1-(toluene-4-sulfonyl)-pyrrolidin-2-yl]-butyl}-1H-[1,2,4]triazole.

41. A compound according to claim 17 wherein $R^3$ is a substituted 5-membered heteroaryl ring containing from 1 to 4 N or O heteroatoms.

42. A compound according to claim 41 wherein said substituted 5-membered heteroaryl ring contains from 1 to 4 nitrogen atoms and n is 2.

43. The compound of claim 42, which is (2RS,5SR)-5-{2-[5-(4-Fluoro-phenyl)-1-(toluene-4-sulfonyl)-pyrrolidin-2-yl]-ethyl}-2-methyl-2H-tetrazole.

44. The compound of claim 42, which is (2RS,5SR)-5-{2-[5-(4-Fluoro-phenyl)-1-(toluene-4-sulfonyl)-pyrrolidin-2-yl]-ethyl}-1-methyl-1H-[1,2,4]triazole.

45. The compound of claim 42, which is (2RS,5SR)-3-{2-[5-(4-Fluoro-phenyl)-1-(toluene-4-sulfonyl)-pyrrolidin-2-yl]-ethyl}-1-methyl-1H-[1,2,4]triazole.

46. The compound of claim 42, which is (2RS,5SR)-2-{2-[5-(4-Fluoro-phenyl)-1-(toluene-4-sulfonyl)-pyrrolidin-2-yl]-ethyl}-5-methyl-2H-tetrazole.

47. The compound of claim 42, which is (2RS,5SR)-1-{2-[5-(4-Fluoro-phenyl)-1-(toluene-4-sulfonyl)-pyrrolidin-2-yl]-ethyl}-5-methyl-1H-tetrazole.

48. The compound of claim 42, which is (2RS,5SR)-1-{2-[5-(4-Fluoro-phenyl)-1-(toluene-4-sulfonyl)-pyrrolidin-2-yl]-ethyl}-4-methyl-1H-imidazole.

49. The compound of claim 42, which is (2RS,5SR)-1-{2-[5-(4-Fluoro-phenyl)-1-(toluene-4-sulfonyl)-pyrrolidin-2-yl]-ethyl}-2-methyl-1H-imidazole.

50. A compound according to claim 41 wherein said substituted 5-membered heteroaryl ring contains from 1 to 4 nitrogen atoms and n is 3, 4 or 5.

51. The compound of claim 50, which is (2RS,5RS)-5-{3-[5-(4-Fluoro-phenyl)-1-(toluene-4-sulfonyl)-pyrrolidin-2-yl]-propyl}-2-methyl-2H-tetrazole.

52. The compound of claim 50, which is (2RS,5RS)-5-{3-[5-(4-Fluoro-phenyl)-1-(toluene-4-sulfonyl)-pyrrolidin-2-yl]-propyl}-1-methyl-1H-tetrazole.

53. The compound of claim 50, which is (2RS,5RS)-5-{4-[5-(4-Fluoro-phenyl)-1-(toluene-4-sulfonyl)-pyrrolidin-2-yl]-butyl}-1-methyl-1H-tetrazole.

54. The compound of claim 50, which is (2RS,5RS)-5-{3-[5-(4-Fluoro-phenyl)-1-(toluene-4-sulfonyl)-pyrrolidin-2-yl]-propyl}-1-methyl-1H-[1,2,4]triazole.

55. The compound of claim 50, which is (2RS,5RS)-3-{3-[5-(4-Fluoro-phenyl)-1-(toluene-4-sulfonyl)-pyrrolidin-2-yl]-propyl}-1-methyl-1H-[1,2,4]triazole.

56. The compound of claim 50, which is (2RS,5RS)-1-{3-[5-(4-Fluoro-phenyl)-1-(toluene-4-sulfonyl)-pyrrolidin-2-yl]-propyl}-4-methyl-1H-imidazole.

57. The compound of claim 50, which is (2RS,5RS)-1-{3-[5-(4-Fluoro-phenyl)-1-(toluene-4-sulfonyl)-pyrrolidin-2-yl]-propyl}-2-methyl-1H-imidazole.

58. The compound of claim 50, which is (2RS,5RS)-2-{3-[5-(4-Fluoro-phenyl)-1-(toluene-4-sulfonyl)-pyrrolidin-2-yl]-propyl}-5-methyl-2H-tetrazole.

59. The compound of claim 50, which is (2RS,5RS)-1-{3-[5-(4-Fluoro-phenyl)-1-(toluene-4-sulfonyl)-pyrrolidin-2-yl]-propyl}-5-methyl-1H-tetrazole.

60. The compound of claim 50, which is (2RS,5RS)-1-{4-[5-(4-Fluoro-phenyl)-1-(toluene-4-sulfonyl)-pyrrolidin-2-yl]-butyl}-4-methyl-1H-imidazole.

61. The compound of claim 50, which is (2RS,5RS)-2-{4-[5-(4-Fluoro-phenyl)-1-(toluene-4-sulfonyl)-pyrrolidin-2-yl]-butyl}-5-methyl-2H-tetrazole.

62. The compound of claim 50, which is (2RS,5RS)-1-{4-[5-(4-Fluoro-phenyl)-1-(toluene-4-sulfonyl)-pyrrolidin-2-yl]-butyl}-5-methyl-1H-tetrazole.

63. A compound according to claim 17 wherein $R^3$ is a substituted 5-membered heteroaryl ring containing from 1 to 4 N or O heteroatoms and containing at least one N atom and at least one O atom.

64. A compound according to claim 63 wherein n is 2.

65. The compound of claim 64, which is (2RS,5SR)-5-{2-[5-(4-Fluoro-phenyl)-1-(toluene-4-sulfonyl)-pyrrolidin-2-yl]-ethyl}-3-methyl-[1,2,4]oxadiazole.

66. The compound of claim 64, which is (2RS,5SR)-5-Cyclopropyl-3-{2-[5-(4-fluoro-phenyl)-1-(toluene-4-sulfonyl)-pyrrolidin-2-yl]-ethyl}-[1,2,4]oxadiazole.

67. The compound of claim 64, which is (2RS,5SR)-3-{2-[5-(4-Fluoro-phenyl)-1-(toluene-4-sulfonyl)-pyrrolidin-2-yl]-ethyl}-5-methyl-[1,2,4]oxadiazole.

68. The compound of claim 64, which is (2RS,5SR)-3-Cyclopropyl-5-{2-[5-(4-fluoro-phenyl)-1-(toluene-4-sulfonyl)-pyrrolidin-2-yl]-ethyl}-[1,2,4]oxadiazole.

69. The compound of claim 64, which is (2RS,5SR)-2-{2-[5-(4-Fluoro-phenyl)-1-(toluene-4-sulfonyl)-pyrrolidin-2-yl]-ethyl}-5-methyl-[1,3,4]oxadiazole.

70. The compound of claim 64, which is (2RS,5SR)-2-[5-(4-Fluoro-phenyl)-1-(toluene-4-sulfonyl)-pyrrolidin-2-yl-methyl]-5-methyl-[1,3,4]oxadiazole.

71. A compound according to claim 63 wherein n is 3, 4 or 5.

72. The compound of claim 71, which is (2RS,5RS)-5-{3-[5-(4-Fluoro-phenyl)-1-(toluene-4-sulfonyl)-pyrrolidin-2-yl]-propyl}-3-methyl-[1,2,4]oxadiazole.

73. The compound of claim 71, which is (2RS,5RS)-2-{3-[5-(4-Fluoro-phenyl)-1-(toluene-4-sulfonyl)-pyrrolidin-2-yl]-propyl}-5-methyl-[1,3,4]oxadiazole.

74. A compound according to claim 17 wherein $R^3$ is an unsubstituted 5-membered heteroaryl ring containing from 1 to 4 N or O heteroatoms and containing at least one N atom and one O atom and wherein n is 3, 4 or 5.

75. The compound of claim 74, which is (2RS,5RS)-2-{3-[5-(4-Fluoro-phenyl)-1-(toluene-4-sulfonyl)-pyrrolidin-2-yl]-propyl}-[1,3,4]oxadiazole.

76. A compound according to claim 17 wherein $R^3$ is —C(O)NR'R".

77. The compound of claim 76, which is (2RS,5SR)-3-[5-(4-Fluoro-phenyl)-1-(toluene-4-sulfonyl)-pyrrolidin-2-yl]-propionamide.

78. The compound of claim 76, which is (2RS,5RS)-5-[5-(4-Fluoro-phenyl)-1-(toluene-4-sulfonyl)-pyrrolidin-2-yl]-pentanoic acid amide.

79. The compound of claim 76, which is (2RS,5RS)-4-[5-(4-Fluoro-phenyl)-1-(toluene-4-sulfonyl)-pyrrolidin-2-yl]-butyramide.

80. A compound according to claim 17 wherein $R^3$ is N-hydroxy-amidino.

81. The compound of claim 80, which is (2RS,5SR)-5-(4-Fluoro-phenyl)-N-hydroxy-1-(toluene-4-sulfonyl)-pyrrolidine-2-carboxamidine.

82. The compound of claim 80, which is (2RS,5SR)-3-[5-(4-Fluoro-phenyl)-1-(toluene-4-sulfonyl)-pyrrolidin-2-yl]-N-hydroxy-propionamidine.

83. The compound of claim 80, which is (2RS,5RS)-4-[5-(4-Fluoro-phenyl)-1-(toluene-4-sulfonyl)-pyrrolidin-2-yl]-N-hydroxy-butyramidine.

84. The compound of claim 80, which is (2RS,5RS)-5-[5-(4-Fluoro-phenyl)-1-(toluene-4-sulfonyl)-pyrrolidin-2-yl]-N-hydroxy-pentanamidine.

85. A compound according to claim 17 wherein $R^3$ is —N(R')—C(O)—$R^4$.

86. The compound of claim 85, which is (2SR,5SR)-N-{3-[5-(4-Fluoro-phenyl)-1-(toluene-4-sulfonyl)-pyrrolidin-2-yl]-propyl}-acetamide.

87. The compound of claim 85, which is (2SR,5SR)-Cyclopropanecarboxylic acid {3-[5-(4-fluoro-phenyl)-1-(toluene-4-sulfonyl)-pyrrolidin-2-yl]-propyl}-amide.

88. The compound of claim 85, which is (2RS,5RS)-N-{3-[5-(4-Fluoro-phenyl)-1-(toluene-4-sulfonyl)-pyrrolidin-2-yl]-propyl}-propionamide.

89. The compound of claim 85, which is (2RS,5RS)-N-{3-[5-(4-Fluoro-phenyl)-1-(toluene-4-sulfonyl)-pyrrolidin-2-yl]-propyl}-2,2-dimethyl-propionamide.

90. The compound of claim 85, which is (2RS,5RS)-Cyclopentanecarboxylic acid {3-[5-(4-fluoro-phenyl)-1-(toluene-4-sulfonyl)-pyrrolidin-2-yl]-propyl}-amide.

91. The compound of claim 85, which is (2RS,5RS)-N-{4-[5-(4-Fluoro-phenyl)-1-(toluene-4-sulfonyl)-pyrrolidin-2-yl]-butyl}-acetamide.

92. The compound of claim 85, which is (2RS,5RS)-Cyclopropanecarboxylic acid {4-[5-(4-fluoro-phenyl)-1-(toluene-4-sulfonyl)-pyrrolidin-2-yl]-butyl}-amide.

93. The compound of claim 85, which is (2RS,5RS)-N-{5-[5-(4-Fluoro-phenyl)-1-(toluene-4-sulfonyl)-pyrrolidin-2-yl]-pentyl}-acetamide.

94. The compound of claim 85, which is (2RS,5RS)-N-{3-[5-(4-Fluoro-phenyl)-1-(toluene-4-sulfonyl)-pyrrolidin-2-yl]-propyl}-benzamide.

95. The compound of claim 85, which is (2RS,5RS)-2,2,2-Trifluoro-N-{3-[5-(4-fluoro-phenyl)-1-(toluene-4-sulfonyl)-pyrrolidin-2-yl]-propyl}-acetamide.

96. The compound of claim 85, which is (2RS,5RS)-N-{3-[5-(4-Fluoro-phenyl)-1-(toluene-4-sulfonyl)-pyrrolidin-2-yl]-propyl}-isobutyramide.

97. A compound according to claim 17 wherein $R^3$ is —N(R')—C(S)—NR'R'" and R' and R'" are as defined above.

98. The compound of claim 97, which is (2RS,5RS)-1-{3-[5-(4-Fluoro-phenyl)-1-(toluene-4-sulfonyl)-pyrrolidin-2-yl]-propyl}-3-methyl-thiourea.

99. A compound according to claim 9 wherein $R^3$ is a dihydro derivative of a 5-membered heteroaryl ring containing from 1 to 4 N or O heteroatoms, which are unsubsituted or substituted by lower alkyl or cycloalkyl; and n is an integer from 2 to 5.

100. The compound of claim 99, which is 3-[5-(4-Fluoro-phenyl)-1-(toluene-4-sulfonyl)-pyrrolidin-2-yl]-5-methyl-4,5-dihydro-[1,2,4]oxadiazole.

101. A compound according to claim 1 having the structure

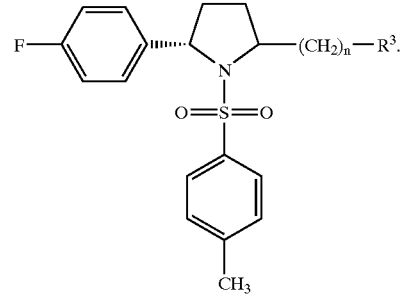

I-C

102. A compound according to claim 101 wherein $R^3$ is —N(R')—C(O)—$R^4$, and n is 2.

103. The compound of claim 102, which is (2RS,5SR)-N-{2-[5-(4-Fluoro-phenyl)-1-(toluene-4-sulfonyl)-pyrrolidin-2-yl]-ethyl}-propionamide.

104. The compound of claim 102, which is (2RS,5SR)-N-{2-[5-(4-Fluoro-phenyl)-1-(toluene-4-sulfonyl)-pyrrolidin-2-yl]-ethyl}-benzamide.

105. The compound of claim 102, which is (2RS,5SR)-Cyclopropanecarboxylic acid {2-[5-(4-fluoro-phenyl)-1-(toluene-4-sulfonyl)-pyrrolidin-2-yl]-ethyl}-amide.

106. The compound of claim 102, which is (2RS,5SR)-N-{2-[5-(4-Fluoro-phenyl)-1-(toluene-4-sulfonyl)-pyrrolidin-2-yl]-ethyl}-acetamide.

107. The compound of claim 102, which is (2R,5S)-3-[5-(4-Fluoro-phenyl)-1-(toluene-4-sulfonyl)-pyrrolidin-2-yl]-propionamide.

108. A compound according to claim 101 wherein $R^3$ is —N(R')—C(O)—$R^4$; wherein $R^4$ and R' are as defined above; and wherein n is 3, 4 or 5.

109. The compound of claim 108, which is (2S,5S)-N-{3-[5-(4-Fluoro-phenyl)-1-(toluene-4-sulfonyl)-pyrrolidin-2-yl]-propyl}-acetamide.

110. The compound of claim 108, which is (2S,5S)-Cyclopropane-carboxylic acid {3-[5-(4-fluoro-phenyl)-1-(toluene-4-sulfonyl)-pyrrolidin-2-yl]-propyl}-amide.

111. A compound according to claim 101 wherein $R^3$ is —C(O)NR'R".

112. The compound of claim 111, which is (2R,5S)-3-[5-(4-Fluoro-phenyl)-1-(toluene-4-sulfonyl)-pyrrolidin-2-yl]-propionamide.

113. A compound according to claim 101 wherein $R^3$ is a 5-membered heteroaryl ring containing from 1 to 4 N or O heteroatoms, said ring being unsubstituted or substituted by lower alkyl or cycloalkyl.

114. A compound according to claim 113 wherein $R^3$ is a substituted 5-membered heteroaryl ring and n is 2.

115. The compound of claim 114, which is (2R,5S)-5-{2-[5-(4-Fluoro-phenyl)-1-(toluene-4-sulfonyl)-pyrrolidin-2-yl]-ethyl}-2-methyl-2H-tetrazole.

116. The compound of claim 114, which is (2R,5S)-5-{2-[5-(4-Fluoro-phenyl)-1-(toluene-4-sulfonyl)-pyrrolidin-2-yl]-ethyl}-1-methyl-1H-tetrazole.

117. The compound of claim 114, which is (2RS,5SR)-2-{2-[5-(4-Fluoro-phenyl)-1-(toluene-4-sulfonyl)-pyrrolidin-2-yl]-ethyl}-1-methyl-1H-imidazole.

118. The compound of claim 114, which is (2R,5S)-2-{2-[5-(4-Fluoro-phenyl)-1-(toluene-4-sulfonyl)-pyrrolidin-2-yl]-ethyl}-1-methyl-1H-imidazole.

119. A compound according to claim 113 wherein $R^3$ is a substituted 5-membered heteroaryl ring and n is 3, 4 or 5.

120. The compound of claim 119, which is (2RS,5RS)-2-{3-[5-(4-Fluoro-phenyl)-1-(toluene-4-sulfonyl)-pyrrolidin-2-yl]-propyl}-1-methyl-1H-imidazole.

121. The compound of claim 119, which is (2S,5S)-5-{3-[5-(4-Fluoro-phenyl)-1-(toluene-4-sulfonyl)-pyrrolidin-2-yl]-propyl}-1-methyl-1H-[1,2,4]triazole.

122. The compound of claim 119, which is (2S,5R)-3-{3-[5-(4-Fluoro-phenyl)-1-(toluene-4-sulfonyl)-pyrrolidin-2-yl]-propyl}-1-methyl-1H-[1,2,4]triazole.

123. A compound according to claim 113 wherein $R^3$ is an unsubstituted 5-membered heteroaryl ring and n is 2.

124. The compound of claim 123, which is (2RS,5SR)-3-[5-(4-Fluoro-phenyl)-1-(toluene-4-sulfonyl)-pyrrolidin-2-yl-methyl]-[1,2,4]oxadiazole.

125. The compound of claim 123, which is (2RS,5SR)-2-{2-[5-(4-Fluoro-phenyl)-1-(toluene-4-sulfonyl)-pyrrolidin-2-yl]-ethyl}-1H-imidazole.

126. The compound of claim 123, which is (2R,5S)-2-{2-[5-(4-Fluoro-phenyl)-1-(toluene-4-sulfonyl)-pyrrolidin-2-yl]-ethyl}-1H-imidazole.

127. The compound of claim 123, which is (2R,5S)-2-{2-[5-(4-Fluoro-phenyl)-1-(toluene-4-sulfonyl)-pyrrolidin-2-yl]-ethyl}-[1,3,4]oxadiazole.

128. A compound according to claim 113 wherein $R^3$ is an unsubstituted 5-membered heteroaryl ring and n is 3, 4 or 5.

129. The compound of claim 128, which is (2RS,5RS)-2-{3-[5-(4-Fluoro-phenyl)-1-(toluene-4-sulfonyl)-pyrrolidin-2-yl]-propyl}-1H-imidazole.

130. The compound of claim 128, which is (2R,5S)-1-{3-[5-(4-Fluoro-phenyl)-1-(toluene-4-sulfonyl)-pyrrolidin-2-yl]-propyl}-1H-[1,2,4]triazole.

131. The compound of claim 128, which is (2S,5S)-1-{3-[5-(4-Fluoro-phenyl)-1-(toluene-4-sulfonyl)-pyrrolidin-2-yl]-propyl}-1H-imidazole.

132. The compound of claim 128, which is (2S,5S)-1-{3-[5-(4-Fluoro-phenyl)-1-(toluene-4-sulfonyl)-pyrrolidin-2-yl]-propyl}-1H-pyrazole.

133. The compound of claim 128, which is (2S,5S)-1-{4-[5-(4-Fluoro-phenyl)-1-(toluene-4-sulfonyl)-pyrrolidin-2-yl]-butyl}-1H-imidazole.

134. The compound of claim 128, which is (2S,5S)-1-{4-[5-(4-Fluoro-phenyl)-1-(toluene-4-sulfonyl)-pyrrolidin-2-yl]-butyl}-1H-[1,2,4]triazole.

135. A pharmaceutical composition comprising a compound of formula I

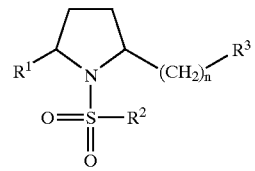

wherein
$R^1$ is aryl, which is unsubstituted or substituted by halogen;
$R^2$ is aryl, which is unsubstituted or substituted by halogen or lower alkyl;
$R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
$R^4$ is cycloalkyl, phenyl or lower alkyl, which is unsubstituted or substituted by halogen
R is lower alkyl;
R' and R'" are lower alkyl or cycloalkyl-lower alkyl;
R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
n is an integer from 2 to 5;
or a pharmaceutically acceptable salt thereof; and at least one pharmaceutically acceptable excipient.

136. A process for the manufacture of a compound of formula I

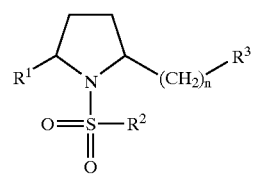

wherein
$R^1$ is aryl, which is unsubstituted or substituted by halogen;
$R^2$ is aryl, which is unsubstituted or substituted by halogen or lower alkyl;
$R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
$R^4$ is cycloalkyl, phenyl or lower alkyl, which is unsubstituted or substituted by halogen
R is lower alkyl;
R' and R'" are lower alkyl or cycloalkyl-lower alkyl;
R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
n is an integer from 2 to 5;
or a pharmaceutically acceptable salt thereof, which process comprises reacting a compound of the formula

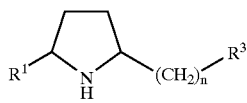

with a compound of formula

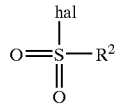

to obtain a compound of formula

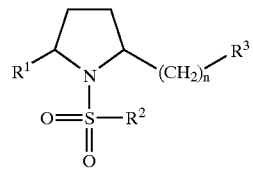

or,
converting a functional group of $R^3$ in a compound of formula I into another functional group,
or,
converting a compound of formula I into a pharmaceutically acceptable salt.

137. The compound according to claim 1 having the following formula

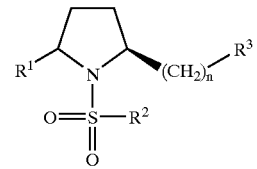

wherein
 $R^1$ is aryl, which is unsubstituted or substituted by halogen;
 $R^2$ is aryl, which is unsubstituted or substituted by halogen or lower alkyl;
 $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
 $R^4$ is cycloalkyl, phenyl or lower alkyl, which is unsubstituted or substituted by halogen
 R is lower alkyl;
 R' and R'" are lower alkyl or cycloalkyl-lower alkyl;
 R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
 n is an integer from 2 to 5;
or a pharmaceutically acceptable salt thereof.

138. A compound according to claim 1 having the following formula

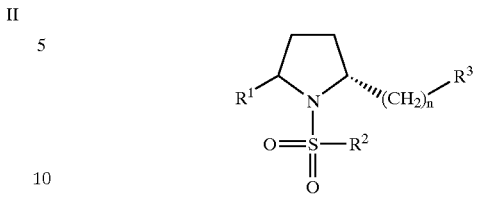

wherein
 $R^1$ is aryl, which is unsubstituted or substituted by halogen;
 $R^2$ is aryl, which is unsubstituted or substituted by halogen or lower alkyl;
 $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
 $R^4$ is cycloalkyl, phenyl or lower alkyl, which is unsubstituted or substituted by halogen
 R is lower alkyl;
 R' and R'" are hydrogen, lower alkyl or cycloalkyl-lower alkyl;
 R" is lower alkyl or lower alkyl substituted by a 5- or 6-membered heteroaryl ring containing from 1 to 4 N or O heteroatoms, said ring being unsubstituted or substituted by lower alkyl or cycloalkyl, and
 n is an integer from 2 to 5;
or a pharmaceutically acceptable salt thereof.

139. A compound according to claim 1 having the following formula

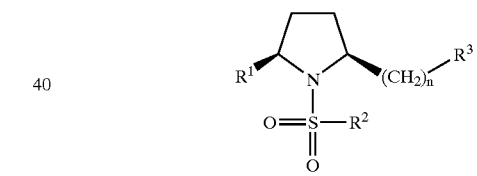

wherein
 $R^1$ is aryl, which is unsubstituted or substituted by halogen;
 $R^2$ is aryl, which is unsubstituted or substituted by halogen or lower alkyl;
 $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
 $R^4$ is cycloalkyl, phenyl or lower alkyl, which is unsubstituted or substituted by halogen
 R is lower alkyl;
 R' and R'" are lower alkyl or cycloalkyl-lower alkyl;
 R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
 n is an integer from 2 to 5;
or a pharmaceutically acceptable salt thereof.

140. A compound according to claim 1 having the following formula

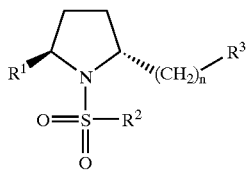

wherein
- $R^1$ is aryl, which is unsubstituted or substituted by halogen;
- $R^2$ is aryl, which is unsubstituted or substituted by halogen or lower alkyl;
- $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
- $R^4$ is cycloalkyl, phenyl or lower alkyl, which is unsubstituted or substituted by halogen
- R is lower alkyl;
- R' and R'" are lower alkyl or cycloalkyl-lower alkyl;
- R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
- n is an integer from 2 to 5;

or a pharmaceutically acceptable salt thereof.

141. A compound according to claim 1 having the following formula

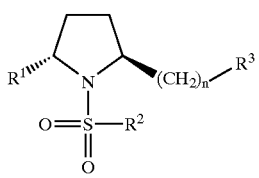

wherein
- $R^1$ is aryl, which is unsubstituted or substituted by halogen;
- $R^2$ is aryl, which is unsubstituted or substituted by halogen or lower alkyl;
- $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
- $R^4$ is cycloalkyl, phenyl or lower alkyl, which is unsubstituted or substituted by halogen
- R is lower alkyl;
- R' and R'" are hydrogen, lower alkyl or cycloalkyl-lower alkyl;
- R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
- n is an integer from 2 to 5;

or a pharmaceutically acceptable salt thereof.

142. A compound according to claim 1 having the following formula

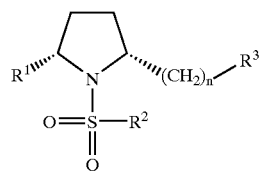

wherein
- $R^1$ is aryl, which is unsubstituted or substituted by halogen;
- $R^2$ is aryl, which is unsubstituted or substituted by halogen or lower alkyl;
- $R^3$ is N-hydroxy-amidino, —C(O)NR'R", —N(R')—C(O)—$R^4$, —N(R')—C(S)—NR'"R or a 5-membered heteroaryl ring containing from 1 to 4 N or O heteroatoms, said ring being unsubstituted or substituted by lower alkyl or cycloalkyl;
- $R^4$ is cycloalkyl, phenyl or lower alkyl, which is unsubstituted or substituted by halogen
- R is lower alkyl;
- R' and R'" are lower alkyl or cycloalkyl-lower alkyl;
- R" is hydrogen, lower alkyl or lower alkyl substituted by a 5- or 6-membered heteroaryl ring containing from 1 to 4 N or O heteroatoms, said ring being unsubstituted or substituted by lower alkyl or cycloalkyl, and
- n is an integer from 2 to 5;

or a pharmaceutically acceptable salt thereof.

143. A compound according to claim 1 wherein $R^3$ is imidazole, pyrazole, [1.2.4]triazole, [1.2.4]oxadiazole, tetrazole, [1.3.4]oxadiazole or oxazole.

144. A compound according to claim 1 wherein $R^3$ is —N(R')—C(O)—$R^4$.

* * * * *